(12) United States Patent
Jenkins

(10) Patent No.: US 10,716,461 B2
(45) Date of Patent: Jul. 21, 2020

(54) EXCHANGEABLE WORKING CHANNEL

(71) Applicant: Auris Health, Inc., Redwood City, CA (US)

(72) Inventor: Thomas R. Jenkins, Alameda, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 15/975,653

(22) Filed: May 9, 2018

(65) Prior Publication Data

US 2018/0333044 A1 Nov. 22, 2018

Related U.S. Application Data

(60) Provisional application No. 62/507,709, filed on May 17, 2017.

(51) Int. Cl.
*A61B 1/00* (2006.01)
*A61B 1/018* (2006.01)
(Continued)

(52) U.S. Cl.
CPC .......... *A61B 1/018* (2013.01); *A61B 1/00059* (2013.01); *A61B 1/00105* (2013.01);
(Continued)

(58) Field of Classification Search
CPC ............ A61B 1/00142; A61B 1/00154; A61B 1/00135; A61B 1/012
(Continued)

(56) References Cited

U.S. PATENT DOCUMENTS 3,572,325 A 3/1971 Bazell et al.
3,913,565 A * 10/1975 Kawahara .......... A61B 1/00082
128/207.15
(Continued)

FOREIGN PATENT DOCUMENTS

CN 101500470 8/2009
CN 102665590 9/2012
(Continued)

OTHER PUBLICATIONS

International Search Report and Written Opinion dated Aug. 8, 2018 in application No. PCT/US18/31850.

*Primary Examiner* — Matthew J Kasztejna
(74) *Attorney, Agent, or Firm* — Knobbe, Martens, Olson & Bear, LLP

(57) ABSTRACT

The systems, methods, and apparatus disclosed herein are directed to an exchangeable working channel for a surgical instrument comprising a proximal portion, a distal portion, and an instrument channel configured to receive the exchangeable working channel. The exchangeable working channel may comprise a shaft comprising a proximal region and a distal region; an inner surface defining a lumen extending through the shaft; and an outer surface configured to interface with the instrument channel of the surgical instrument. The exchangeable working channel may further comprise one or more locking members configured to releasably couple to the proximal portion or the distal portion of the surgical instrument. The exchangeable working channel may increase a service life of the surgical instrument as a worn working channel can be exchanged with a new one.

21 Claims, 10 Drawing Sheets

(51) Int. Cl.
  *A61B 1/12* (2006.01)
  *G02B 23/24* (2006.01)
(52) U.S. Cl.
  CPC .......... *A61B 1/00128* (2013.01); *A61B 1/121* (2013.01); *G02B 23/2476* (2013.01)
(58) Field of Classification Search
  USPC ................................ 600/121–125, 127, 129
  See application file for complete search history.

(56) References Cited

U.S. PATENT DOCUMENTS

| | | | | |
|---|---|---|---|---|
| 4,294,234 A * | 10/1981 | Matsuo | ..................... | A61B 1/07 385/117 |
| 4,392,485 A * | 7/1983 | Hiltebrandt | ........ | A61B 1/00195 600/153 |
| 4,607,619 A * | 8/1986 | Seike | ..................... | A61B 1/018 600/106 |
| 4,690,175 A | 9/1987 | Ouchi et al. | | |
| 4,706,656 A * | 11/1987 | Kuboto | .............. | A61B 1/00135 600/153 |
| 4,741,326 A * | 5/1988 | Sidall | ................. | A61B 1/00091 600/123 |
| 4,745,908 A | 5/1988 | Wardle | | |
| 4,748,969 A | 6/1988 | Wardle | | |
| 4,750,475 A * | 6/1988 | Yoshihashi | ............ | A61B 10/04 600/131 |
| 4,771,766 A * | 9/1988 | Aoshiro | ................. | A61B 1/121 600/155 |
| 4,846,791 A * | 7/1989 | Hattler | ............... | A61M 25/0026 604/43 |
| 4,869,238 A | 9/1989 | Opie et al. | | |
| 4,906,496 A * | 3/1990 | Hosono | ..................... | F16L 9/18 428/36.9 |
| 4,907,168 A | 3/1990 | Boggs | | |
| 4,967,732 A * | 11/1990 | Inoue | ................. | A61B 1/00137 600/139 |
| 5,050,585 A * | 9/1991 | Takahashi | .......... | A61B 1/00073 600/123 |
| 5,083,549 A | 1/1992 | Cho et al. | | |
| 5,106,387 A | 4/1992 | Kittrell et al. | | |
| 5,108,800 A * | 4/1992 | Koo | .......................... | A41G 1/00 156/61 |
| 5,125,909 A * | 6/1992 | Heimberger | ...... | A61M 25/0054 138/121 |
| 5,168,864 A | 12/1992 | Shockey | | |
| 5,217,002 A | 6/1993 | Katsurada | | |
| 5,251,611 A | 10/1993 | Zehel | | |
| 5,257,617 A * | 11/1993 | Takahashi | .......... | A61B 1/00142 600/123 |
| 5,261,391 A * | 11/1993 | Inoue | ..................... | A61B 1/018 600/139 |
| 5,287,861 A | 2/1994 | Wilk | | |
| 5,313,934 A | 5/1994 | Wiita et al. | | |
| 5,386,818 A * | 2/1995 | Schneebaum | .......... | A61B 1/018 600/104 |
| 5,448,988 A | 9/1995 | Watanabe | | |
| 5,478,330 A | 12/1995 | Imran et al. | | |
| 5,482,029 A | 1/1996 | Sekiguchi | | |
| 5,489,270 A | 2/1996 | van Erp | | |
| 5,507,725 A | 4/1996 | Savage et al. | | |
| 5,533,985 A | 7/1996 | Wang | | |
| 5,580,200 A | 12/1996 | Fullerton | | |
| 5,681,296 A * | 10/1997 | Ishida | ................ | A61M 25/0009 600/585 |
| 5,704,534 A | 1/1998 | Huitema et al. | | |
| 5,720,775 A | 2/1998 | Lamard | | |
| 5,741,429 A | 4/1998 | Donadio, III | | |
| 5,749,889 A * | 5/1998 | Bacich | ............... | A61B 17/3417 600/104 |
| 5,873,817 A | 2/1999 | Kokish et al. | | |
| 5,876,325 A | 3/1999 | Mizuno et al. | | |
| 5,879,287 A * | 3/1999 | Yoshihashi | ........ | A61B 1/00142 600/121 |
| 5,882,347 A * | 3/1999 | Mouris-Laan | .... | A61M 25/0023 604/103.09 |
| 5,888,191 A * | 3/1999 | Akiba | ................ | A61B 1/00105 600/153 |
| 5,910,129 A | 6/1999 | Koblish et al. | | |
| 5,938,586 A * | 8/1999 | Wilk | ..................... | A61B 1/121 600/121 |
| 6,012,494 A | 1/2000 | Balazs | | |
| 6,143,013 A | 11/2000 | Samson et al. | | |
| 6,157,853 A | 12/2000 | Blume et al. | | |
| 6,197,015 B1 | 3/2001 | Wilson | | |
| 6,198,974 B1 | 3/2001 | Webster, Jr. | | |
| 6,315,715 B1 | 11/2001 | Taylor et al. | | |
| 6,404,497 B1 | 6/2002 | Backman | | |
| 6,436,107 B1 | 8/2002 | Wang et al. | | |
| 6,464,632 B1 * | 10/2002 | Taylor | .................... | A61B 1/005 138/174 |
| 6,485,411 B1 | 11/2002 | Konstorum | | |
| 6,491,626 B1 | 12/2002 | Stone et al. | | |
| 6,537,205 B1 * | 3/2003 | Smith | ..................... | A61B 1/015 600/104 |
| 6,554,793 B1 | 4/2003 | Pauker et al. | | |
| 6,716,178 B1 | 4/2004 | Kilpatrick et al. | | |
| 6,746,422 B1 | 6/2004 | Noriega | | |
| 6,749,560 B1 | 6/2004 | Konstorum | | |
| 6,790,173 B2 | 9/2004 | Saadat | | |
| 6,827,710 B1 * | 12/2004 | Mooney | .............. | A61B 17/3417 604/167.06 |
| 6,827,712 B2 | 12/2004 | Tovey et al. | | |
| 6,837,846 B2 | 1/2005 | Jaffe | | |
| 6,908,428 B2 * | 6/2005 | Aizenfeld | .......... | A61B 1/00142 600/121 |
| 6,921,362 B2 * | 7/2005 | Ouchi | ................ | A61B 1/00142 600/121 |
| 6,958,035 B2 * | 10/2005 | Friedman | ........... | A61B 1/00082 600/121 |
| 7,008,401 B2 | 3/2006 | Thompson et al. | | |
| 7,130,700 B2 | 10/2006 | Gardeski et al. | | |
| 7,594,903 B2 | 9/2009 | Webler et al. | | |
| 7,645,230 B2 * | 1/2010 | Mikkaichi | .......... | A61B 1/00135 600/121 |
| 7,645,231 B2 * | 1/2010 | Akiba | ................. | A61B 1/00068 600/132 |
| 7,789,827 B2 | 9/2010 | Landry | | |
| 7,930,065 B2 | 4/2011 | Larkin et al. | | |
| 8,052,636 B2 | 11/2011 | Moll et al. | | |
| 8,246,536 B2 * | 8/2012 | Ochi | ..................... | A61B 1/0055 600/123 |
| 8,444,637 B2 | 5/2013 | Podmore et al. | | |
| 8,498,691 B2 | 7/2013 | Moll et al. | | |
| 8,515,215 B2 | 8/2013 | Younge et al. | | |
| 8,652,030 B2 | 2/2014 | Matsuura et al. | | |
| 8,758,231 B2 | 6/2014 | Bunch et al. | | |
| 8,827,947 B2 | 9/2014 | Bosman et al. | | |
| 9,186,046 B2 | 11/2015 | Ramamurthy et al. | | |
| 9,427,551 B2 | 8/2016 | Leeflang et al. | | |
| 9,504,604 B2 | 11/2016 | Alvarez | | |
| 9,561,083 B2 | 2/2017 | Yu et al. | | |
| 9,591,990 B2 | 3/2017 | Chen et al. | | |
| 9,622,827 B2 | 4/2017 | Yu et al. | | |
| 9,636,184 B2 | 5/2017 | Lee et al. | | |
| 9,713,509 B2 | 7/2017 | Schuh et al. | | |
| 9,727,963 B2 | 8/2017 | Mintz et al. | | |
| 9,737,371 B2 | 8/2017 | Romo et al. | | |
| 9,737,373 B2 | 8/2017 | Schuh | | |
| 9,744,335 B2 | 8/2017 | Jiang | | |
| 9,763,741 B2 | 9/2017 | Alvarez et al. | | |
| 9,788,910 B2 | 10/2017 | Schuh | | |
| 9,818,681 B2 | 11/2017 | Machida | | |
| 9,844,353 B2 | 12/2017 | Walker et al. | | |
| 9,844,412 B2 | 12/2017 | Bogusky et al. | | |
| 9,867,635 B2 | 1/2018 | Alvarez et al. | | |
| 9,918,681 B2 | 3/2018 | Wallace et al. | | |
| 9,931,025 B1 | 4/2018 | Graetzel et al. | | |
| 9,949,749 B2 | 4/2018 | Noonan et al. | | |
| 9,955,986 B2 | 5/2018 | Shah | | |

(56) References Cited

U.S. PATENT DOCUMENTS

| | | |
|---|---|---|
| 9,962,228 B2 | 5/2018 | Schuh et al. |
| 10,016,900 B1 | 7/2018 | Meyer et al. |
| 10,022,192 B1 | 7/2018 | Ummalaneni |
| 10,130,427 B2 | 11/2018 | Tanner et al. |
| 10,145,747 B1 | 12/2018 | Lin et al. |
| 10,159,532 B1 | 12/2018 | Ummalaneni et al. |
| 2001/0004676 A1* | 6/2001 | Ouchi ............... A61B 1/00133 600/106 |
| 2003/0036748 A1 | 2/2003 | Cooper et al. |
| 2003/0130564 A1* | 7/2003 | Martone ............ A61B 1/00071 600/121 |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0054322 A1 | 3/2004 | Vargas |
| 2004/0138525 A1 | 7/2004 | Saadat et al. |
| 2004/0193013 A1 | 9/2004 | Isakawa et al. |
| 2004/0249246 A1 | 12/2004 | Campos |
| 2005/0004515 A1 | 1/2005 | Hart et al. |
| 2005/0125005 A1 | 6/2005 | Fujikura |
| 2005/0154262 A1 | 7/2005 | Banik et al. |
| 2005/0159646 A1 | 7/2005 | Nordstrom et al. |
| 2005/0222581 A1* | 10/2005 | Fischer, Jr. ........ A61B 1/00135 606/108 |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Chen |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2009/0099420 A1 | 4/2009 | Woodley et al. |
| 2009/0163851 A1 | 6/2009 | Holloway |
| 2009/0247880 A1 | 10/2009 | Naruse et al. |
| 2009/0254083 A1 | 10/2009 | Wallace et al. |
| 2009/0262109 A1 | 10/2009 | Markowitz et al. |
| 2009/0299344 A1 | 12/2009 | Lee et al. |
| 2009/0306587 A1 | 12/2009 | Milijasevic et al. |
| 2010/0030023 A1 | 2/2010 | Yoshie |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0217184 A1 | 8/2010 | Koblish et al. |
| 2010/0249497 A1 | 9/2010 | Peine et al. |
| 2010/0249506 A1 | 9/2010 | Prisco et al. |
| 2011/0009863 A1 | 1/2011 | Stanislaw |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0261183 A1 | 10/2011 | Ma et al. |
| 2011/0306836 A1 | 12/2011 | Ohline et al. |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0046313 A1 | 2/2014 | Pederson et al. |
| 2014/0142591 A1 | 5/2014 | Alvarez et al. |
| 2014/0200402 A1* | 7/2014 | Snoke .................. A61B 17/42 600/104 |
| 2014/0276391 A1 | 9/2014 | Yu |
| 2014/0276594 A1 | 9/2014 | Tanner et al. |
| 2014/0309649 A1 | 10/2014 | Alvarez et al. |
| 2014/0316397 A1 | 10/2014 | Brown |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0031950 A1* | 1/2015 | Drontle .............. A61B 1/00165 600/104 |
| 2015/0051592 A1 | 2/2015 | Kintz |
| 2015/0101442 A1 | 4/2015 | Romo |
| 2015/0119638 A1 | 4/2015 | Yu et al. |
| 2015/0164594 A1 | 6/2015 | Romo et al. |
| 2015/0164596 A1 | 6/2015 | Romo |
| 2015/0335480 A1 | 11/2015 | Alvarez et al. |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0151122 A1 | 6/2016 | Alvarez et al. |
| 2016/0227982 A1 | 8/2016 | Takahashi |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0346049 A1 | 12/2016 | Allen et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0281218 A1 | 10/2017 | Timm |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |

(56) References Cited

U.S. PATENT DOCUMENTS

| | | |
|---|---|---|
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0228528 A1 | 4/2019 | Mintz et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0307987 A1 | 10/2019 | Yu |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054405 A1 | 2/2020 | Schuh |
| 2020/0054408 A1 | 2/2020 | Schuh et al. |
| 2020/0060516 A1 | 2/2020 | Baez |

FOREIGN PATENT DOCUMENTS

| | | |
|---|---|---|
| EP | 0 543 539 | 5/1993 |
| EP | 0 776 739 | 6/1997 |
| EP | 1 442 720 | 8/2004 |
| EP | 0 904 796 | 11/2004 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | WO 94/14494 | 7/1994 |
| WO | WO 00/67640 | 11/2000 |
| WO | WO 02/074178 | 9/2002 |
| WO | WO 04/039273 | 5/2004 |
| WO | WO 04/105849 | 12/2004 |
| WO | WO 05/032637 | 4/2005 |
| WO | WO 05/081202 | 9/2005 |
| WO | WO 09/097461 | 6/2007 |
| WO | WO 07/146987 | 12/2007 |
| WO | WO 08/097540 | 8/2008 |
| WO | WO 09/092059 | 7/2009 |
| WO | WO 10/081187 | 7/2010 |
| WO | WO 10/088187 | 8/2010 |
| WO | WO 11/005335 | 1/2011 |
| WO | WO 13/107468 | 7/2013 |
| WO | WO 15/093602 | 12/2013 |
| WO | WO 16/003052 | 1/2016 |

* cited by examiner

EXCHANGEABLE WORKING CHANNEL

CROSS-REFERENCE TO RELATED APPLICATION

This application claims the benefit of U.S. Provisional Application No. 62/507,709, filed May 17, 2017, which is hereby incorporated by reference in its entirety.

TECHNICAL FIELD

The present disclosure relates generally to medical devices, and more particularly to an exchangeable working channel for a surgical and/or medical instrument.

BACKGROUND

Medical procedures may involve manipulation of a tool positioned remotely from the operator. For example, the tool may be advanced through a working channel of a surgical instrument (e.g., catheters, endoscopes, etc.) through which the tool is inserted into the body of a patient. In one example, the surgical instrument may be used in the context of minimally invasive surgery, during which medical tools may be inserted into a patient's body through an incision or orifice to access and/or treat tissue. In another example, the surgical instrument may be used in procedures such as biopsies and endoscopy. The surgical instrument may comprise an interior lumen (e.g., a working channel) providing a pathway to the tissue site. Catheters and various tools, such as, for example, a grasping forcep, a biopsy forcep, a cytology brush, a balloon dilator, a snare, a needle, and/or a basket, can be inserted through the working channel of the surgical instrument to access the tissue site.

SUMMARY

The systems, methods and devices of this disclosure each have several innovative aspects, no single one of which is solely responsible for the desirable attributes disclosed herein.

One aspect relates to a removable working channel of a surgical instrument, the surgical instrument having a proximal portion, a distal portion, and a working channel sheath configured to receive the removable working channel, the removable working channel comprising: a shaft, comprising: a proximal region and a distal region; an inner surface defining a lumen extending through the shaft; and an outer surface configured to interface with the working channel sheath of the surgical instrument; and a first locking member at the proximal region of the shaft, the first locking member configured to releasably couple to the proximal portion of the surgical instrument. In some implementations, the surgical instrument may comprise an endoscope.

In some implementations, the first locking member comprises at least one of a clamp, a friction fit component, a latch, a snap fit component, a screw lock, a luer fit, a threaded fit component, a slip fit component, a bayonet, a ball spring or pogo latch, a detent, a magnet, and an O-ring component.

Some implementations further comprise a second locking member at the distal region of the shaft, the second locking member configured to releasably couple to the distal portion of the surgical instrument. In some implementations, the second locking member comprises an annular ring or a spring clamp at the distal region of the shaft. In some implementations, the second locking member comprises at least one of a clamp, a friction fit component, a latch, a snap fit component, a screw lock, a luer fit, a threaded fit component, a slip fit component, a bayonet, a ball spring or pogo latch, a detent, a magnet, and an O-ring component. In some implementations, the removable working channel does not comprise a locking member at the distal region of the shaft.

In some implementations, the first locking member comprises a locking component configured to engage with a tool; and the first locking member is configured to be releasable from the proximal portion of the surgical instrument when, in use, the tool engages and actuates the locking component of the first locking member.

Some implementations further comprise at least one identification member configured to store data comprising information regarding a source of the removable working channel. In some implementations, the at least one identification member comprises a radio-frequency identification (RFID) tag.

In some implementations, the shaft is made of extruded plastic. In some implementations, the shaft is made of at least one of polyether block amide (PEBA), Nylon, polytetrafluoroethylene (PTFE), high-density polyethylene (HDPE), low-density polyethylene (LDPE), linear low density poly ethylene (LLDPE), polyvinyl chloride (PVC), polystyrene, acrylonitrile butadiene styrene (ABS), polypropylene (PP), thermoplastic elastomers (TPE), fluorinated ethylene propylene (FEP), acetal copolymer, polysulfone, polyetheretherketone (PEEK), polyetherimide, polyphenylene oxide (PPO), perfluoroalkoxy (PFA) plastic, polyvinylidene fluoride (PVDF), ethylene tetrafluoroethylene (ETFE), ethylene chlorotrifluoroethylene (ECTFE), and tetrafluoroethylene/hexafluoropropylene/vinylidene fluoride (THV) copolymer. In some implementations, the shaft further comprises an inner liner attached to the inner surface. In some implementations, the inner liner is made of PTFE, HDPE, LDPE, LLDPE, or hydrophilic materials.

In some implementations, the shaft comprises a reinforcement member disposed at least partially between the inner surface and the outer surface. In some implementations, the reinforcement member comprises at least one of (i) one or more coils, (ii) one or more braids, and (iii) one cable tube.

In some implementations, an outer diameter of the shaft is greater than or equal to about 1.2 mm and less than or equal to about 6 mm. In some implementations, an outer diameter of the shaft is about 3.2 mm.

Another aspect relates to an surgical instrument configured to receive a removable working channel, the surgical instrument comprising: a proximal portion and a distal portion; an instrument channel extending through the proximal and distal portions, the instrument channel comprising: a proximal region and a distal region; and an inner surface defining a lumen extending through the instrument channel; a working channel sheath attached to the inner surface of the instrument channel and configured to interface with the removable working channel; and a first coupling member at the proximal portion of the surgical instrument, the first coupling member configured to releasably couple to a proximal region of the removable working channel.

Some implementations further comprise a second coupling member at the distal portion of the surgical instrument, the second coupling member configured to releasably couple to a distal region of the removable working channel. In some implementations, the working channel sheath is made of extruded plastic. In some implementations, the working channel sheath is made of PEBA, Nylon, PTFE, HDPE, LDPE, LLDPE, PVC, polystyrene, ABS, PP, TPE, FEP, acetal copolymer, polysulfone, PEEK, PPO, PFA plastic, PVDF, ETFE, ECTFE, and THV copolymer. In some implementations, the working channel sheath comprises an inner liner made of PTFE, HDPE, LDPE, or LLDPE.

In some implementations, the working channel sheath comprises at least one of (i) one or more coils, (ii) one or more braids, and (iii) one cable tube. In some implementations, the coils, the braids, or the cable tubes are at least partially made of stainless steel, copper, other metals, Nitinol alloy, graphite, polyparaphenylene terephthalamide, Ultra-high-molecular-weight polyethylene (UHMWPE), PEEK, or nylon.

Some implementations further comprises at least one detector configured to read data from at least one identification member of the removable working channel, the data comprising information regarding a source of the removable working channel.

Yet another aspect relates to a tool configured to adjust an attachment between a removable working channel and a surgical instrument, the removable working channel having proximal and distal regions, the surgical instrument having proximal and distal portions, the tool comprising: an actuator configured to engage and actuate at least one of (i) one or more locking members at the proximal region of the removable working channel and (ii) one or more coupling members at the proximal portion of the surgical instrument, wherein, in use, the engagement and actuation of the at least one of (i) one or more locking members and (ii) one or more coupling members by the actuator facilitates at least one of locking and unlocking the attachment between the removable working channel and the surgical instrument.

Still another aspect relates to a method for sanitizing one or more removable working channels of a surgical instrument, the method comprising: removing a first removable working channel from the surgical instrument; analyzing an integrity of the first removable working channel; cleaning and reinstalling the first removable working channel in an instrument channel of the surgical instrument in response to the integrity of the first removable working channel being uncompromised; and replacing the first removable working channel with a second removable working channel in the instrument channel in response to the integrity of the first removable working channel being compromised.

In some implementations, the one or more removable working channels further comprise at least one identification member configured to store data comprising information regarding a source of the one or more removable working channels. In some implementations, the at least one identification member comprises a radio-frequency identification (RFID) tag. Some implementations further comprise updating the identification member with data regarding whether the first removable working channel or the second removable working channel is installed in the instrument channel of the surgical instrument. In some implementations, the one or more removable working channels are made of extruded plastic.

In some implementations, removing the first removable working channel from the surgical instrument comprises removing the first removable working channel through a proximal end of the instrument. In some implementations, replacing the first removable working channel with the second removable working channel comprises inserting a distal end of the second removable working channel through a proximal end of the instrument channel until the distal end of the second removable working channel reaches near a distal end of the instrument channel.

In some implementations, the surgical instrument comprises: a proximal portion and a distal portion; an instrument channel extending through the proximal and distal portions; a working channel sheath attached to an inner surface of the instrument channel; and one or more coupling members at the proximal portion or the distal portion of the surgical instrument.

In some implementations, the one or more coupling members comprise at least one of a clamp, a friction fit component, a latch, a snap fit component, a screw lock, a luer fit, a threaded fit component, a slip fit component, a bayonet, a ball spring or pogo latch, a detent, a magnet, and an O-ring component. In some implementations, the surgical instrument comprises an endoscope.

In some implementations, the one or more removable working channels further comprise one or more locking members configured to releasably couple to the one or more coupling members of the surgical instrument.

In some implementations, removing the first removable working channel from the surgical instrument comprises: engaging a tool to at least one of (i) the one or more coupling members of the surgical instrument and (ii) the one or more locking members of the first removable working channel; actuating the tool to release the one or more coupling members of the surgical instrument from the one or more locking members of the first removable working channel; and removing the first removable working channel from the surgical instrument.

In some implementations, replacing the first removable working channel with a second removable working channel comprises inserting a distal end of the second removable working channel through a proximal end of the instrument channel until at least one of the one or more coupling members of the surgical instrument engage with at least one of the one or more locking members of the second removable working channel.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

DETAILED DESCRIPTION

Introduction

Figure 1A:
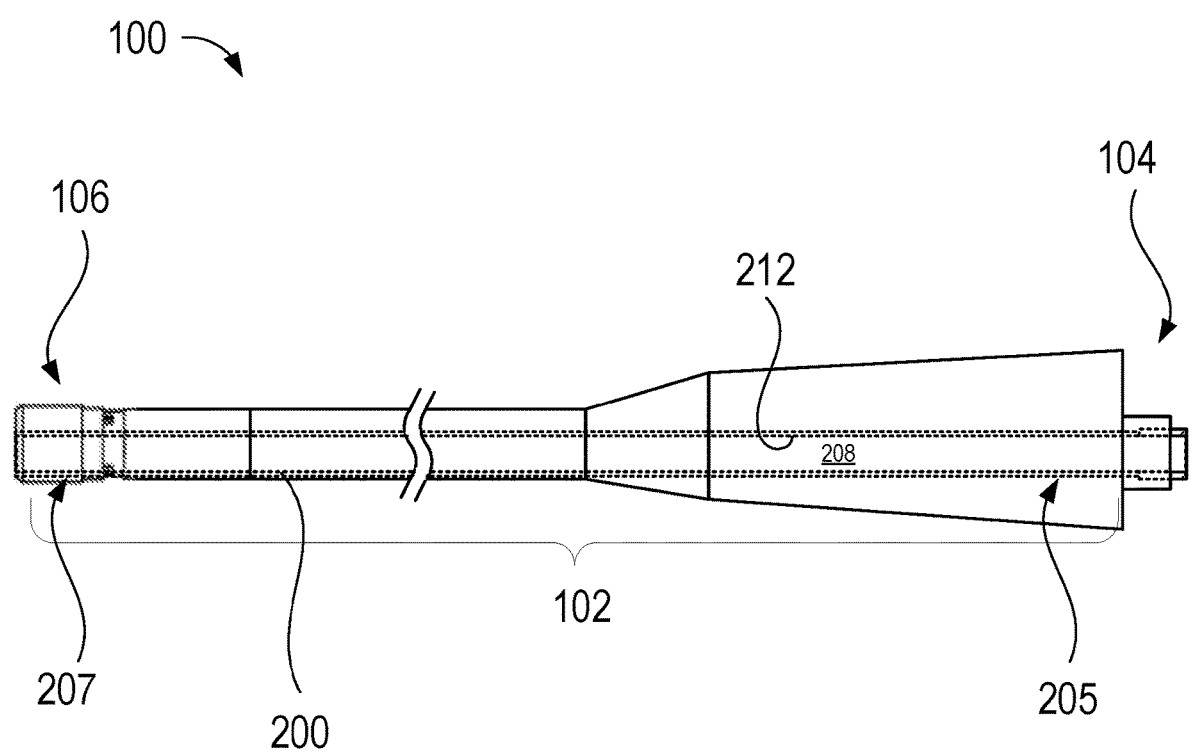
FIGS. 1A-1E illustrate an embodiment of a surgical instrument including a removable working channel in accordance with one or more aspects as described herein.

During a medical procedure (e.g., minimally invasive surgery) using a surgical instrument (e.g., a catheter, endoscope, laparoscope, etc.) comprising an instrument channel, medical tools, such as, for example, cannulas, graspers, forceps, scissors, retractors, and/or stabilizers may be inserted through the instrument channel of the surgical instrument to reach a target organ or tissue. Components of these medical tools may be made of, for example, stainless steel, tungsten, other metals, or other rigid materials. As a result, when a medical tool passes through the instrument channel of the surgical instrument, the medical tool may scratch, deform, or otherwise damage the inner surface of the instrument channel. Over repeated uses of the surgical instrument, interaction between the medical tools and the inner surface of the instrument channel can result in wear and tear of the inner surface of the instrument channel. Thus, in some cases, the service life of the surgical instrument may be limited by the service life of the instrument channel of the surgical instrument.

The present disclosure relates to removable working channel(s) that may be installed or removed from the instrument channel of the surgical instrument. The removable working channel may be configured to be installed inside the instrument channel of the surgical instrument and to at least partially cover the inner surface of the instrument channel. When the removable working channel is worn enough to warrant replacement, the worn working channel can be exchanged with a new working channel. Thus, the disclosed removable working channel can provide an improved service life of the surgical instrument.

The disclosed systems and apparatuses can provide advantages for medical procedures and applications, including but not limited to surgeries that involve the use of endoscopic, laparoscopic, and/or catheter-delivered tools. Thus, though the disclosed removable working channels are described in portions of the present disclosure below within the context of endoscopy, it should be understood that such removable working channels can also be used with other surgical instruments and in other types of procedures in order to provide the disclosed benefits. For example, a removable working channel as described herein can be used in other types of instruments including but not limited to a bronchoscope, a sinuscope (e.g., as used in sinusplasty), a nasopharyngoscope, a laryngoscope, a laparoscope, a gastroscope, a colonoscope, a hysteroscope, a cystoscope, a uroscope, a urethroscope, a cardioscope (e.g., as used in heart catheterization), and an arthroscope, and more generally in procedures that involve delivering tools through flexible and/or curved scopes, catheters, or tubes (collectively referred to as endoscopes, for simplicity of describing the various embodiments discussed herein).

As used herein, "distal" refers to a relative position or location a scope, instrument, or tool that is positioned closer to the patient during use, and "proximal" refers to a relative position or location of the scope, instrument, or tool positioned closer to the operator (e.g., a physician or robotic control system). Stated differently, the relative positions of components of the scope, instrument, tool, and/or the robotic system are described herein from the vantage point of the operator, going from a proximal location to a distal location.

As used herein, the terms "about" or "approximately" refer to a range of measurements of a length, thickness, a quantity, time period, or other measurable values. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

Example Surgical Instrument and Removable Working Channel

Figure 1B:
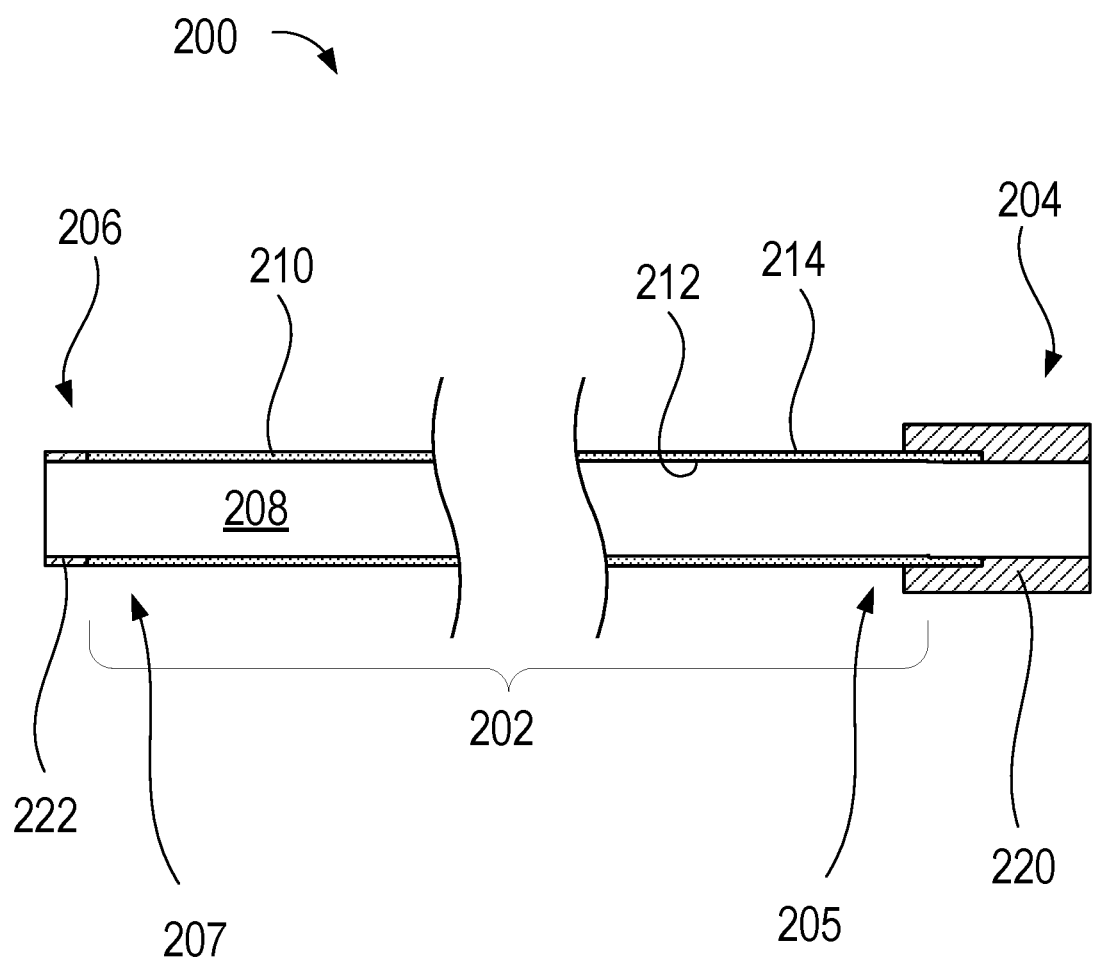
Figure 1C:
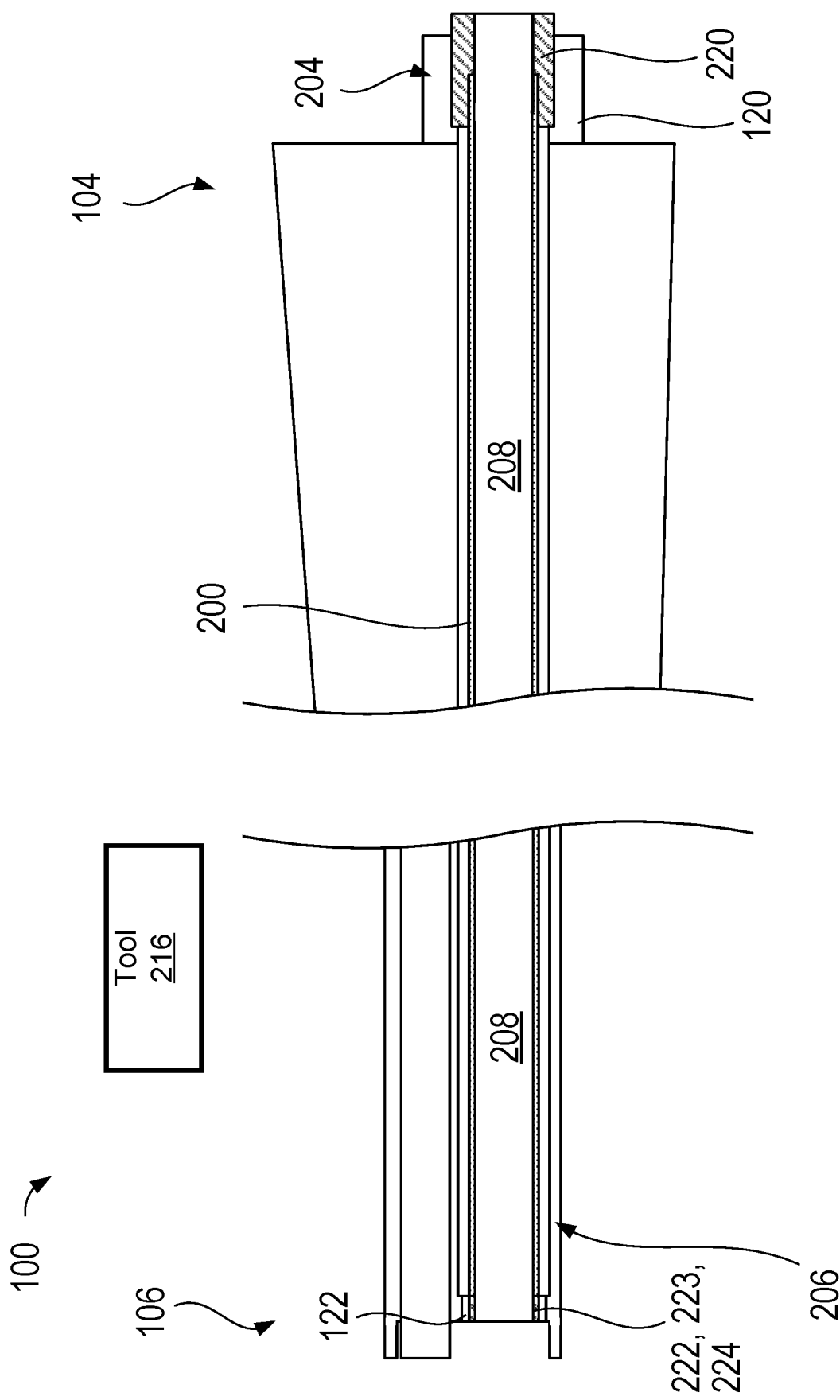
Figure 1D:
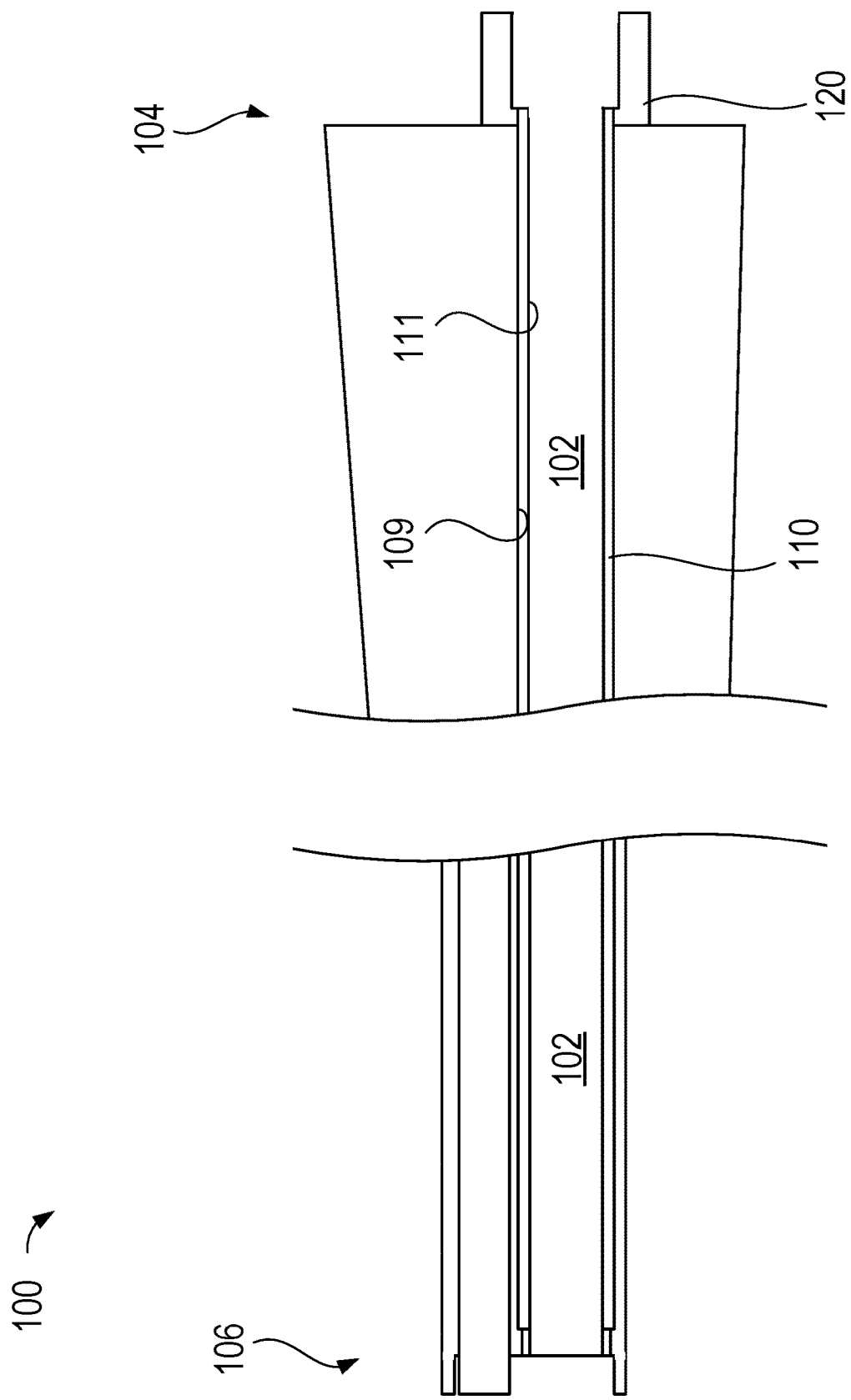
Figure 1E:
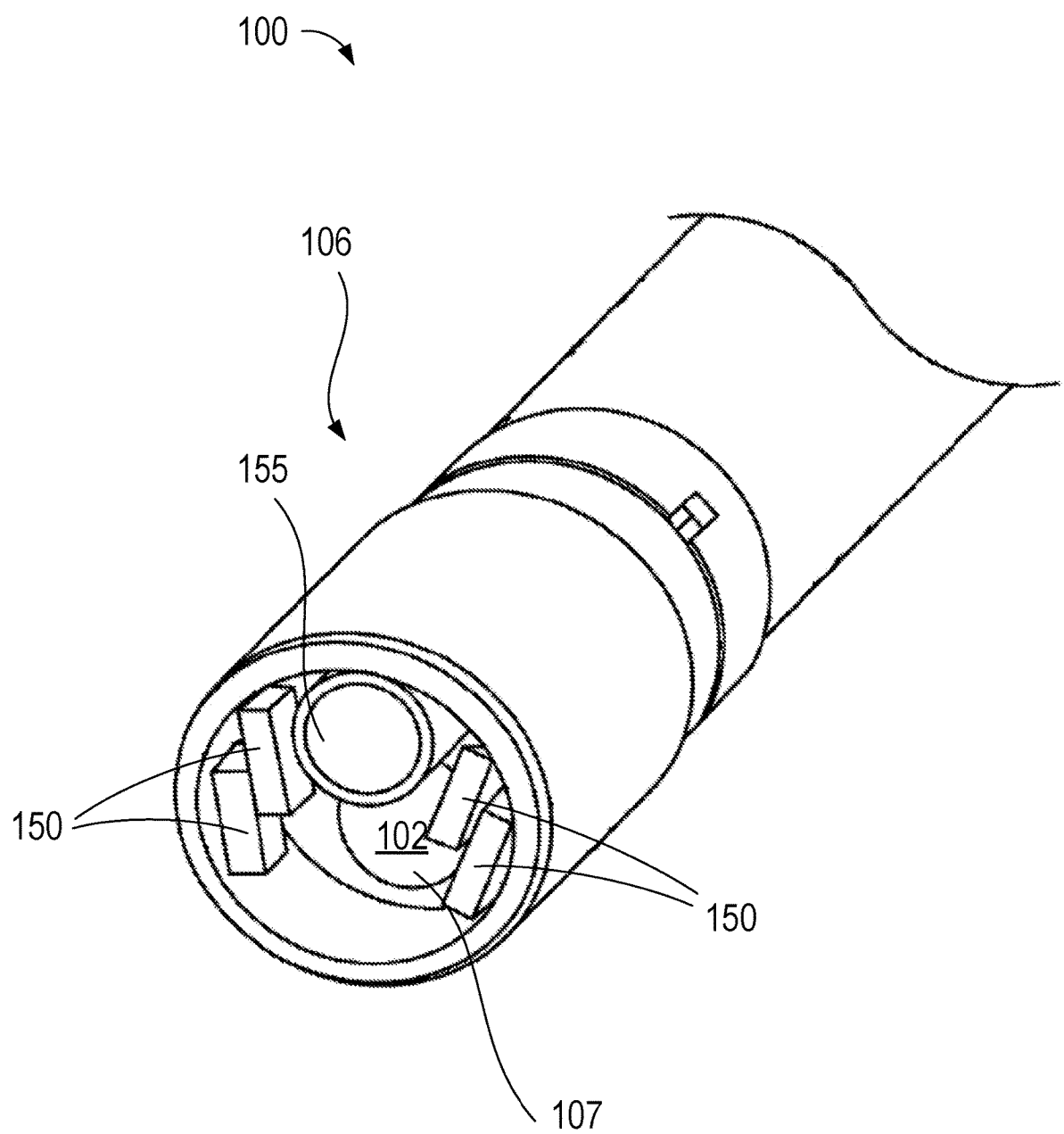

FIGS. 1A-1E illustrate an embodiment of a surgical instrument 100 including a removable working channel 200. FIG. 1A illustrates a side view of the surgical instrument 100. FIG. 1B illustrates a cross-sectional view of the removable working channel 200. FIG. 1C illustrates a cross-sectional view of a proximal portion 104 and a distal portion 106 of the surgical instrument 100, with the removable working channel 200 positioned within the surgical instrument 100. FIG. 1D illustrates a cross-sectional view of the proximal portion 104 and the distal portion 106 of the surgical instrument 100, with the removable working channel 200 removed from the surgical instrument 100. FIG. 1E illustrates a perspective view of a distal portion 106 of the surgical instrument 100. FIGS. 1A-1E are discussed together in portions of the description below due to the overlap of depicted features.

With reference to FIG. 1A, there is shown an example surgical instrument 100 that includes a proximal portion 104 and a distal portion 106 and may include at least one instrument channel 102 extending therethrough. The surgical instrument 100 may further comprise one or more coupling members (not shown here but described in greater detail below) at or near the proximal portion 104 and/or the distal portion 106 of the surgical instrument 100. Though the surgical instrument 100 disclosed in FIG. 1A is described within the context of endoscopic procedures, it will be appreciated that the surgical instrument 100 may include other types of instruments suitable for types of medical procedures. As noted above, examples of the surgical instrument 100 include but are not limited to an endoscope, a bronchoscope, a sinuscope, a nasopharyngoscope, a laryngoscope, a laparoscope, a gastroscope, a colonoscope, a hysteroscope, a cystoscope, a uroscope, a urethroscope, a cardioscope, an arthroscope, etc.

In some embodiments, the instrument channel 102 may have a diameter ranging from about 1.2 mm to about 6 mm. More specifically, the instrument channel 102 may have a diameter about 2.8 mm, about 3.7 mm, about 4.2 mm, and about 6 mm. In some embodiments, the instrument channel 102 may be substantially straight along its longitudinal axis, as illustrated in FIG. 1A. In other embodiments, at least a portion of the instrument channel 102 may be curved. It is to be appreciated that the shape of the instrument channel 102 may depend on how the surgical instrument 100 is actuated or flexed.

As shown in FIG. 1A, the instrument channel 102 of the surgical instrument 100 is configured to receive a removable working channel 200 (drawn with dotted lines to indicate that the removable working channel 200 is inside the surgical instrument 100) such that the removable working channel 200 can be inserted into and/or removed from the instrument channel 102. The removable working channel 200 may be installed within the instrument channel 102 such that an outer surface of the removable working channel 200 interfaces the inner surface of the instrument channel 102. The removable working channel 200, when installed within the instrument channel 102, protects the inner surface of the instrument channel 102 from wear and tear caused by medical tools when passed through the surgical instrument 100.

As shown, the removable working channel 200 includes a proximal region 205, a distal region 207, and an inner surface 212 defining a lumen 208. The lumen 208 of the removable working channel 200 may be a working area usable for the passage of intraoperative instruments, generally referred to herein as medical tools. In other embodiments (not illustrated), one or more additional channels may be incorporated to provide further capabilities, such as, for example, flush/irrigation, aspiration, illumination, laser energy, etc. The lumen 208 of the removable working channel 200 may also be configured to deliver a variety of therapeutic substances along with a tool configured to pass through the removable working channel 200. These substances may be delivered precisely to a target site using the insertion, articulation, and/or other capabilities of the surgical instrument 100 of the present disclosure.

With reference to FIG. 1B, there is shown a cross-sectional view of the removable working channel 200 introduced in FIG. 1A. The removable working channel 200 comprises a shaft 202 and may further comprise one or more locking members 220 and 222 at or near a proximal region 204 and at or near a distal region 206 of the removable working channel 200, respectively. As used herein, the phrase "locking member" may refer to a mechanism for securing the removable working channel to the surgical instrument. The shaft 202 includes the proximal region 205, the distal region 207, and the lumen 208 extending therethrough. The shaft 202 includes a wall 210 comprising the inner surface 212 and an outer surface 214. The inner surface 212 of the shaft 202 defines the lumen 208 extending along the longitudinal length of the shaft 202.

The outer diameter of the shaft 202 may be substantially similar to, equal to, or less than the inner diameter of the instrument channel 102 of the surgical instrument 100. One example of the removable working channel 200 can define a shaft having an outer diameter that is greater than or equal to about 1.2 mm, or less than or equal to about 6 mm. In another example, the removable working channel 200 may have a shaft having an outer diameter of about 3.2 mm. The thickness of the shaft wall 210 may be greater than or equal to about 0.1 mm or less than or equal to about 0.3 mm.

In some embodiments, the shaft 202 of the removable working channel 200 may be made of plastic materials or extruded plastic. For example, the shaft 202 may be made of at least one of polyether block amide (PEBA), Nylon, and polytetrafluoroethylene (PTFE), high-density polyethylene (HDPE), low-density polyethylene (LDPE), linear low density poly ethylene (LLDPE), polyvinyl chloride (PVC), polystyrene, acrylonitrile butadiene styrene (ABS), polypropylene (PP), thermoplastic elastomers (TPE), fluorinated ethylene propylene (FEP), acetal copolymer, polysulfone, polyetheretherketone (PEEK), polyetherimide, polyphenylene oxide (PPO), perfluoroalkoxy (PFA) plastic, polyvinylidene fluoride (PVDF), ethylene tetrafluoroethylene (ETFE), ethylene chlorotrifluoroethylene (ECTFE), tetrafluoroethylene/hexafluoropropylene/vinylidene fluoride (THV) copolymer, or other similar medical grade extrusions. Additionally or alternatively, the shaft 202 may be at least partially made of one or more compressible materials. That way, when the removable working channel 200 is inserted into the surgical instrument 100, the removable working channel 200 may be collapsible or compressible to facilitate the insertion.

In some embodiments, the shaft 202 of the removable working channel 200 may further comprise an inner liner (not shown) attached to the inner surface 212 of the shaft 202. The inner liner may be made of at least one of PTFE, HDPE, LDPE, or LLDPE, or other similar medical grade extrusions. The inner liner may reduce friction and facilitate the passing of medical instruments through the lumen 208 of the removable working channel 200. A lubricant may be added to the surface of the inner liner or the inner surface 212 of the removable working channel 200 to further reduce friction between the surface of the inner liner or the inner surface 212 and the medical instruments.

In one embodiment, the shaft 202 may further comprise a reinforcement member disposed at least partially between the inner surface 212 and the outer surface 214 of the shaft 202. In another embodiment, the reinforcement member may be disposed inside the inner surface 212 of the shaft 202 or outside the outer surface 214 of the shaft 202. Examples of the reinforcement member include one or more coils, one or more braids, or one or more cable tubes. The coils, the braids, and/or the cable tubes may be at least partially made of stainless steel (e.g., stainless steel 304 or stainless steel 316), copper, other metals, Nitinol alloy, graphite, or polymers such as polyparaphenylene terephthalamide (e.g., tradename Kevlar), Ultra-high-molecular-weight polyethylene (UHMWPE) (e.g., tradename Spectra), PEEK, or nylon. It is to be appreciated that other materials may be used depending on the application and the materials just described are not provided in a limiting manner.

As described above with reference to FIG. 1B, the removable working channel 200 may further comprise the one or more locking members 220 at or near the proximal region 204 of the removable working channel 200. The one or more locking members 220 may be configured to releasably couple with the surgical instrument (not shown; see e.g., the surgical instrument 100 in FIG. 1A). As shown in FIG. 1B, the one or more locking members 220 may be at the proximal end of the removable working channel 200. In other examples, the one or more locking members 220 may be placed anywhere in the proximal region 204 of the removable working channel 200.

Similarly, the removable working channel 200 may further comprise the one or more locking members 222 at or near the distal region 206 of the removable working channel 200. The one or more locking members 222 may be configured to releasably couple with the surgical instrument (not shown). As shown in FIG. 1B, the one or more locking members 222 may be at the distal end of the removable working channel 200. In other examples, the one or more locking members 222 may be placed anywhere in the distal region 206 of the removable working channel 200.

With reference to FIG. 1C, there is shown a cross-sectional view of the surgical instrument 100 and the removable working channel 200 inside the surgical instrument 100. The removable working channel 200 is configured to be installed within the surgical instrument 100. The one or more locking members 220 at the proximal end of the removable working channel 200 may be configured to releasably couple with the one or more coupling members 120 of the surgical instrument 100. In another embodiment in which the surgical instrument 100 does not comprise one or more coupling members 120 at or near the proximal portion 104 (not shown), the one or more locking members 220 may be configured to releasably couple to the proximal portion 104 of the surgical instrument 100.

Similarly, the one or more locking members 222 at the distal end of the removable working channel 200 may be configured to releasably couple with the one or more coupling members 122 of the surgical instrument 100. In another embodiment in which the surgical instrument 100 does not comprise one or more coupling members 122 at or near the distal portion 106 (not shown), the one or more locking members 220 may be configured to releasably couple to the distal portion 106 of the surgical instrument 100.

The locking members 220 and 222 of the removable working channel 200 on the proximal region 204 and the distal region 206, respectively, may comprise a removable luer fit component 223, a clamp, a friction fit component (also known as interference fit), a latch, a threaded fit component 224, a slip fit component, a bayonet, a ball spring or pogo latch, a detent, a magnet, a screw lock, a snap fit component, or an O-ring component.

In one example, the locking members 220 and/or 222 may comprise a removable luer fit component configured to fit into a complementary removable luer fit component of the surgical instrument 100. In another example, the locking members 220 and/or 222 may comprise a clamp configured to removably hold at least a portion of the surgical instrument 100 (e.g., proximal portion 104 or distal portion 106). In yet another example, the locking members 220 and/or 222 may comprise a friction fit component configured to slip into the instrument channel 102 of the surgical instrument 100 and lock by friction with the inner surface of the instrument channel 102. In still another example, the locking members 220 and/or 222 may comprise a latch configured to join or fasten to a latch component of the surgical instrument 100 or directly to a portion of the surgical instrument 100. The latch may comprise (1) a ball with a spring or (2) a pogo latch.

In one example, the locking members 220 and/or 222 may comprise a threaded fit component configured to rotatably fit and lock into the instrument channel 102 of the surgical instrument 100 via an interlocking between threads of the threaded fit component and those on the inner surface of the instrument channel 102. In one example, the locking members 220 and/or 222 may comprise a slip fit component configured to fit and lock into the instrument channel 102 of the surgical instrument 100. In another example, the locking members 220 and/or 222 may comprise a bayonet component. The bayonet component may comprise a catch, a detent, or a pin configured to removably couple to a receptor (e.g., a hole, a groove, or an L-shaped groove) on the inner surface of the instrument channel 102 of the surgical instrument 100. Alternatively, the bayonet component of the removable working channel 200 may be a receptor (e.g., a hole, a groove, or an L-shaped groove) configured to receive a catch, a detent, or a pin on the inner surface of the instrument channel 102 of the surgical instrument 100. In yet another example, the locking members 220 and/or 222 may comprise a magnet configured to interact with a magnet at or near the instrument channel 102 of the surgical instrument 100. In still another example, the locking members 220 and/or 222 may comprise a screw lock configured to rotatably lock the removable working channel 200 to the surgical instrument 100 via an interlocking between threads of the screw lock and those on the surgical instrument 100. In another example, the locking members 220 and/or 222 may comprise an O-ring component configured to be placed inside and seal against the instrument channel 102 of the surgical instrument 100.

In some embodiments, the locking members 220 and/or 222 of the removable working channel 200 may comprise one or more locking components configured to engage with a tool 216. The locking members 220 and/or 222 may be releasable from the surgical instrument 100 when, in use, the tool 216 engages and actuates the locking components. In another embodiment, the tool 216 may be configured to selectively actuate and release certain type or types of the locking components. For example, the tool 216 may be a key that is configured to engage and unlock only one type of the locking components. The key may be configured such that the key is not able to engage or unlock other types of the locking components. In yet another embodiment, the tool 216 may be configured to wirelessly communicate with the locking components to actuate them.

As described above with reference to FIG. 1C, the surgical instrument 100 is configured to receive the removable working channel 200. The surgical instrument 100 may further comprise one or more coupling members 122 at or near the distal portion 106 of the surgical instrument 100. The one or more coupling members 122 of the surgical instrument 100 may be configured to releasably couple with the one or more locking members 222 of the removable working channel 200. In another embodiment in which the removable working channel 200 does not comprise one or more locking members at or near the distal region 206 of the removable working channel 200 (not shown), the one or more coupling members 122 may be configured to releasably couple to the distal region 206 of the removable working channel 200. Examples of the coupling members 122 of the surgical instrument 100 are explained below.

As shown in FIG. 1C, the one or more coupling members 122 may be at the distal end of the surgical instrument 100. In other embodiments, the one or more coupling members 122 may be placed anywhere in the distal portion 106 of the surgical instrument 100.

Similarly, the surgical instrument 100 may further comprise one or more coupling members 120 at or near the proximal portion 104 of the surgical instrument 100. The one or more coupling members 120 of the surgical instrument 100 may be configured to releasably couple with the one or more locking members 220 of the removable working channel 200. In another embodiment in which the removable working channel 200 does not comprise one or more locking members at or near the proximal region 204 of the removable working channel 200 (not shown), the one or more coupling members 120 may be configured to releasably couple to the proximal region 204 of the removable working channel 200. For example, the one or more coupling members 120 may comprise a clamp mechanism configured to couple to or pinch at the proximal region 204 of the removable working channel 200.

As shown in FIG. 1C, the one or more coupling members 120 may be at the proximal end of the surgical instrument 100. In other embodiments, the one or more coupling members 120 may be placed anywhere in the proximal portion 104 of the surgical instrument 100.

The coupling members 120 and 122 on the proximal portion 104 and the distal portion 106, respectively, of the surgical instrument 100 may comprise a removable luer fit component, a clamp, a friction fit component (also known as an interference fit component), a latch, a threaded fit component, a slip fit component, a bayonet, a ball spring or pogo latch, a detent, a magnet, a screw lock, a snap fit component, or an O-ring component. In one example, the coupling members 120 and/or 122 of the surgical instrument 100 may comprise a removable luer fit component configured to fit into a complementary removable luer fit component of the removable working channel 200. In another example, the coupling members 120 and/or 122 may comprise a clamp configured to removably hold at least a portion of the removable working channel 200. In yet another example, the coupling members 120 and/or 122 may comprise a friction fit component configured to lock by friction with the outer surface of the removable working channel 200. In still another example, the coupling members 120 and/or 122 may comprise a latch configured to join or fasten to a latch component of the removable working channel 200 or directly to a portion of the removable working channel 200. The latch may comprise (1) a ball with a spring and/or (2) a pogo latch.

In one example, the coupling members 120 and/or 122 may comprise a threaded fit component configured to rotatably fit and lock with the removable working channel 200 via an interlocking between threads of the threaded fit component and those on the outer surface of the removable working channel 200. In one example, the coupling members 120 and/or 122 may comprise a slip fit component configured to fit and lock with the removable working channel 200. In another example, the coupling members 120 and/or 122 may comprise a bayonet component. The bayonet component may comprise a catch, a detent, or a pin configured to removably couple to a receptor (e.g., a hole, a groove, or an L-shaped groove) on the outer surface of the removable working channel 200. Alternatively, the bayonet component of the surgical instrument 100 may be a receptor (e.g., a hole, a groove, or an L-shaped groove) configured to receive a catch, a detent, or a pin on the outer surface of the removable working channel 200. In yet another example, the coupling members 120 and/or 122 may comprise a magnet configured to interact with a magnet placed on the removable working channel 200. In still another example, the coupling members 120 and/or 122 may comprise a screw lock configured to rotatably lock at least a portion of the surgical instrument 100 to at least a portion of the removable working channel 200 via an interlocking between threads of the screw lock and those on the removable working channel 200. In another example, the coupling members 120 and/or 122 may comprise an O-ring component configured to be seal against the removable working channel 200.

In some embodiments, the coupling members 120 and/or 122 of the surgical instrument 100 may comprise one or more locking components configured to engage with a tool 216. The coupling members 120 and/or 122 of the surgical instrument 100 may be configured to be released from the removable working channel 200 when the tool 216 engages and actuates the locking components of the coupling members 120 and/or 122. In another embodiment, the tool 216 may be configured to selectively actuate and release certain type or types of the locking components. For example, the tool 216 may be a key that is configured to engage and unlock only one type of the locking components. The key may be configured such that the key is not able to engage or unlock other types of the locking components. In yet another embodiment, the tool 216 may wirelessly communicate with the locking components to actuate them.

The surgical instrument 100 may comprise a sensor and/or a detector configured to communicate with a processor (e.g., of a surgical robotic system or a computing device in communication with the surgical robotic system) configured to process or verify the information received from the at least one identification member of the removable working channel 200. The user of the surgical instrument 100 (e.g., an operator, a physician, or a robotic surgical system) may set requirements as to which removable working channel 200 may be installed to the surgical instrument 100. After the processor receives information from the removable working channel 200 (e.g., from the sensor or detector), the processor may determine whether the removable working channel 200 satisfies the requirements set by the user. The surgical instrument 100 may be configured to only receive a removable working channel 200 whose information is verified by the processor. In some embodiments, the surgical instrument 100 may be configured to receive only removable working channels 200 whose information satisfies a certain set of requirements set by the user. For example, the surgical instrument 100 may be configured to receive removable working channels 200 produced by verifiable manufacturers only or by a certain set of one or more manufacturers only. In another embodiment, the surgical instrument 100 may be configured to receive only removable working channels 200 that have not been used before. In yet another embodiment, the processor may be configured to transmit a message or otherwise warn a user that one or more requirements of the removable working channel 200 have not been met (e.g., if the source or the manufacturer of the removable working channel 200 is not verifiable).

With reference to FIG. 1D, there is shown a cross-sectional view of the proximal portion 104 and the distal portion 106 of the surgical instrument 100, with the removable working channel 200 removed from the surgical instrument 100. As shown in FIG. 1D, at least a portion of the inner surface 109 of the instrument channel 102 may be covered by a working channel sheath 110. The working channel sheath 110 may be configured to receive the removable working channel 200 as described herein. The removable working channel 200 may be positioned inside the surgical instrument 100 such that the outer surface of the removable working channel 200 interfaces the inner surface 111 of the working channel sheath 110. The working channel sheath 110 may reduce friction between the inner surface 109 of the instrument channel 102 and the removable working channel 200, facilitating the installation and/or removal processes for the removable working channel 200. In other embodiments (not shown), the inner surface 109 of the instrument channel 102 may not be covered with the working channel sheath 110.

The working channel sheath 110 may be made of plastic or extruded plastic. In another embodiment, the working channel sheath 110 may be made of at least one of PEBA, Nylon, PTFE, HDPE, LDPE, LLDPE, PVC, polystyrene, ABS, PP, TPE, FEP, acetal copolymer, polysulfone, PEEK, polyetherimide, PPO, PFA plastic, PVDF, ETFE, ECTFE, and THV copolymer, or other similar medical grade extrusions. In another embodiment, the working channel sheath 110 may further comprise an inner liner attached to the inner surface 111 of the working channel sheath 110. The inner liner may be made of at least one of PTFE, HDPE, LDPE, LLDPE, or other similar medical grade extrusions, or hydrophilic materials. The hydrophilic inner liner coating may be useful for some applications such as tissue/stone removal or easing the passage of medical tools.

The working channel sheath 110 may further comprise one or more coils, one or more braids, or one or more cable tubes. The coils, the braids, and/or the cable tubes may be at least partially inside the working channel sheath 110. In another embodiment, the coils, the braids, and/or the cable tubes may be disposed inside the inner surface 111 of the working channel sheath 110 or outside the outer surface of the working channel sheath 110. The coils, the braids, and/or the cable tubes may be at least partially made of stainless steel (e.g., stainless steel 304 or stainless steel 316), copper, other metals, Nitinol alloy, graphite, or polymers such as polyparaphenylene terephthalamide (e.g., tradename Kevlar), UHMWPE (e.g., tradename Spectra), PEEK, or nylon.

It is to be appreciated that other materials may be used depending on the application and the materials just described are not provided in a limiting manner.

Referring to FIG. 1E, the distal portion 106 of the surgical instrument 100 may comprise the distal region 107 of the instrument channel 102, light sources 150 (e.g., light emitting diode (LED), optic fiber, etc.), and a camera 155 (e.g., charge-coupled device (CCD) or complementary metal-oxide-semiconductor (CMOS) camera, terminal end of imaging fiber bundle etc.). In conjunction with the light sources 150, the camera 155 may be used, for example, to capture real-time video to assist with navigation within anatomical structures. Other channels or operating electronics may be provided along the surgical instrument 100 to provide various known capabilities at the distal portion 106, such as wiring to the camera 155, insufflation, suction, electricity, fiber optics, ultrasound transducer, electromagnetic (EM) sensing, and optical coherence tomography (OCT) sensing.

Other Examples of Surgical Instruments and Removable Working Channels

Figure 2A:
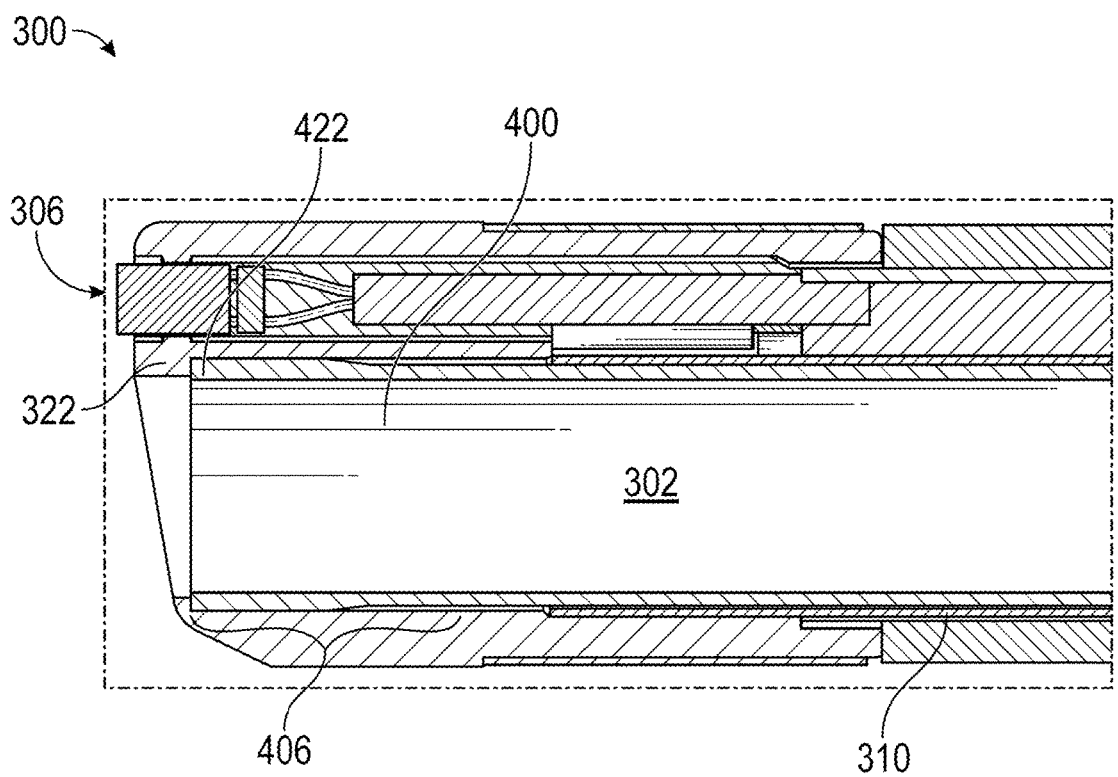
FIGS. 2A-2B illustrate another embodiment of a surgical instrument including a removable working channel in accordance with one or more aspects as described herein.
Figure 2B:
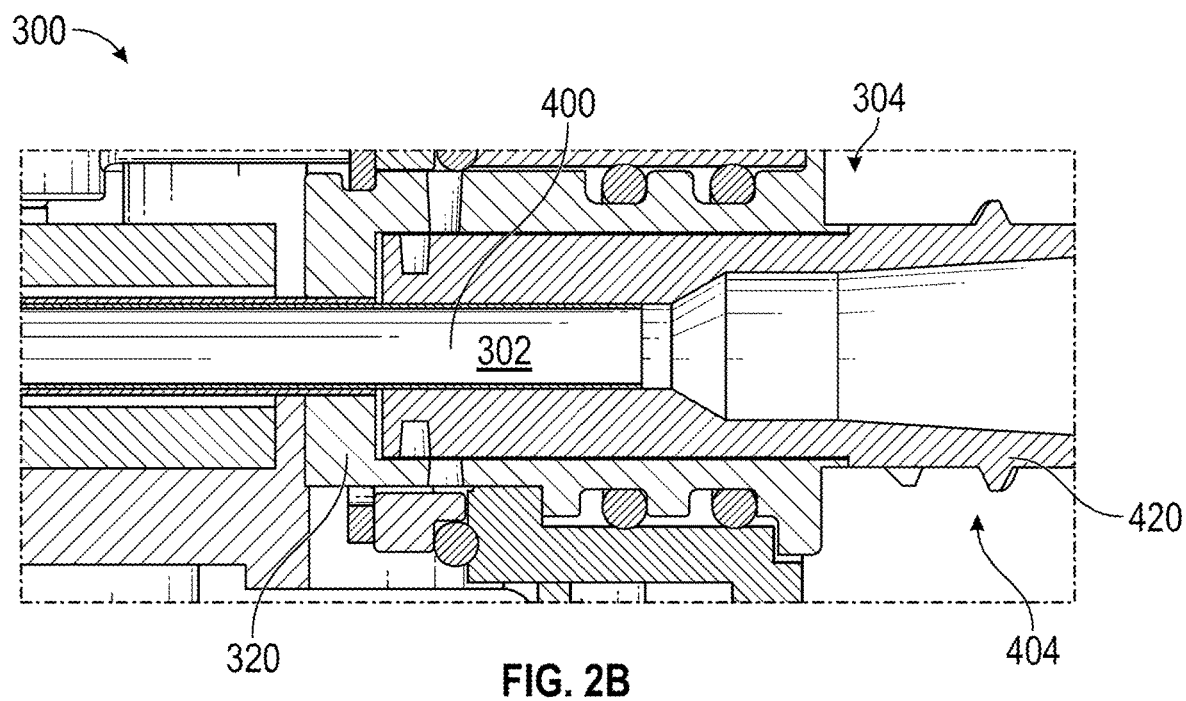

FIGS. 2A-2B illustrate aspects of another embodiment of a surgical instrument 300 including a removable working channel 400 as described herein, wherein the surgical instrument 300 comprises an endoscope and includes (1) a removable luer adapter 320 at the proximal portion 304 of the surgical instrument 300 and (2) a snap fit component 322 at the distal portion 306 of the surgical instrument 300; and the removable working channel 400 comprises (1) a removable luer component 420 at the proximal region 404 of the removable working channel 400 and (2) a snap fit component 422 at the distal region 406 of the removable working channel 400. FIG. 2A illustrates a cross-sectional view of a distal portion 306 of the surgical instrument 300. FIG. 2B illustrates a cross-sectional view of a proximal portion 304 of the surgical instrument 300. FIGS. 2A-2B are discussed together in portions of the description below due to the overlap of depicted features.

In FIGS. 2A-2B, components that can be similar to components described above with reference the embodiment of FIGS. 1A-1E and the description above are identified by similar numbers wherein the reference number used is preceded by the numbers "3" and "4" instead of "1" and "2", respectively. For example, components 302, 304 and 306 can be similar to components 102, 104 and 106, and components 402, 404 and 406 can be similar to components 202, 204 and 206. Reference can be made to the description above for additional descriptions and embodiments of these components which can be used with the embodiment of FIGS. 2A-2B.

Similar to the surgical instrument 100 of FIGS. 1A-1E, the surgical instrument 300 may include at least one instrument channel 302 extending along its longitudinal length. With reference to FIG. 2A, there is shown an embodiment of the surgical instrument 300 comprising an endoscope. The instrument channel 302 of the surgical instrument 300 is configured to receive a removable working channel 400 such that the removable working channel 400 can be inserted into, positioned within, attached to, and/or removed from the instrument channel 302.

Similar to the surgical instrument 100 of FIGS. 1A-1E, at least a portion of the inner surface of the instrument channel 302 of the surgical instrument 300 may be covered with a working channel sheath 310. An outer surface of the working channel sheath 310 interfaces with the inner surface of the instrument channel 302, and an inner surface of the working channel sheath 310 interfaces with the instrument channel 302. The working channel sheath 310 is configured to receive the removable working channel 400 as described herein.

With reference to the embodiment of FIG. 2A, the surgical instrument 300 includes a snap fit component 322 near the distal end of the surgical instrument 300. It is noted that the snap fit component 322 may be placed anywhere in the distal portion 306 of the surgical instrument 300. The snap fit component 322 comprises a step portion configured to abut a distal region 406 of the removable working channel 400. At the distal portion 306 of the surgical instrument 300, the diameter of the instrument channel 302 increases such that the distal portion of the instrument channel 302 can receive the distal region 406 of the removable working channel 400. The removable working channel 400 comprises a snap fit component 422 near the distal end of the removable working channel 400. It is noted that the snap fit component 422 may be placed anywhere in the distal region 406 of the removable working channel 400. The snap fit component 422 is configured to annularly surround the outer surface of the distal region 406 of the removable working channel 400. That way, the outer diameter of the removable working channel 400 at its distal region 406 is greater than that at other regions of the removable working channel 400. As shown in FIG. 2A, the snap fit component 422 may be integrally formed to the distal region 406 of the removable working channel 400. It is to be appreciated that an interference fit component and/or a slip fit component may be used in the distal portion 306 of the surgical instrument 300 instead of or in addition to the snap fit component 322 for simplicity.

The snap fit component 422 of the removable working channel 400 is configured to releasably couple to the snap fit component 322 of the surgical instrument 300. The outer diameter of the distal region 406 of the removable working channel 400 is greater than the diameter of the instrument channel 302 at or near its proximal end. Thus, when the removable working channel 400 is inserted into a proximal end of the instrument channel 302, the distal region 406 of the removable working channel 400 is folded toward the radially inward direction in order for the removable working channel 400 to be able to pass through the instrument channel 302. To facilitate the insertion, the removable working channel 400 may be at least partially made of one or more compressible materials. In some embodiments, when inserting the removable working channel 400 into a proximal end of the instrument channel 302, the user may use a tool (e.g., a mandrel with a handle) to move the removable working channel 400 into the instrument channel 302. When the snap fit component 422 of the removable working channel 400 reaches the distal portion 306 of the surgical instrument 300, the diameter of the instrument channel 302 becomes greater to be substantially similar to the outer diameter of the distal region 406 of the removable working channel 400. As a result, the distal region 406 of the removable working channel 400 radially expands from its folded state to conform to the shape of the instrument channel 302 at the distal portion 306. When the snap fit component 422 of the removable working channel 400 slides along the instrument channel 302 further distally, the distal region 406 of the removable working channel 400 abuts the step portion of the snap fit component 322 of the surgical instrument 300, which prevents a further distal movement of the removable working channel 400.

In some embodiments, the snap fit component 322 of the surgical instrument 300 may comprise an annular recess on an inner surface at or near the distal end of the instrument channel 302, and the snap fit component 422 of the removable working channel 400 may comprise an annular ring on its outer surface. The annular ring of the removable working channel 400 may be configured to snap into and removably couple with the annular recess of the instrument channel 302. In other embodiments, the snap fit component 422 of the removable working channel 400 may comprise a spring clamp on its outer surface. The spring clamp of the removable working channel 400 may be configured to snap into and removably couple with the annular recess of the instrument channel 302. In other embodiments, the snap fit component 322 of the surgical instrument 300 may comprise a wire spring clamp embedded at or near the distal end of the instrument channel 302 (e.g., on the inner surface at or near the distal end of the instrument channel 302). The wire spring clamp may be configured to removably hold the distal region 406 of the removable working channel 400.

The releasable coupling between the two snap fit components 322 and 422 is at least partially achieved by friction between the inner surface of the instrument channel 302 at or near the distal portion 306 and the snap fit component 422 of the removable working channel 400. When the removable working channel 400 is removed from the instrument channel 302 in a proximal direction, the snap fit component 422 of the removable working channel 400 slides in a proximal direction, so the diameter of the instrument channel 302 contacting the snap fit component 422 becomes smaller. As a result, the snap fit component 422 of the removable working channel 400 is forced into the portion of the instrument channel 302 outside the distal region 406 whose diameter is smaller than the outer diameter of the distal region 406 of the removable working channel 400. Accordingly, the snap fit component 422 of the removable working channel 400 is pushed against the inner surface of the instrument channel 302, causing frictions resisting the uncoupling between the two snap fit components 322 and 422. However, the coupling between the two snap fit components 322 and 422 is not permanent and may be released by enough pulling force and/or manipulation of the distal region 406 of the removable working channel 400 (e.g., pulling the distal region 406 toward the radially inward direction) that overcomes the forces of the snap fit. In some embodiments, one or more tools may be used to remove the removable working channel 400 from the instrument channel 302.

With reference to FIG. 2B, the removable working channel 400 comprises a removable luer component 420 at the proximal region 404 of the removable working channel 400. The surgical instrument 300 includes a removable luer adapter 320 at the proximal portion 304 of the surgical instrument 300. The removable luer component 420 of the removable working channel 400 is configured to releasably couple to the removable luer adapter 320 of the surgical instrument 300. The removable luer component 420 of the removable working channel 400 may be configured to slip and fit into the removable luer adapter 320 of the surgical instrument 300. Alternatively, the removable luer component 420 of the removable working channel 400 may be configured to rotatably fit and lock into the removable luer adapter 320 of the surgical instrument 300.

Figure 3A:
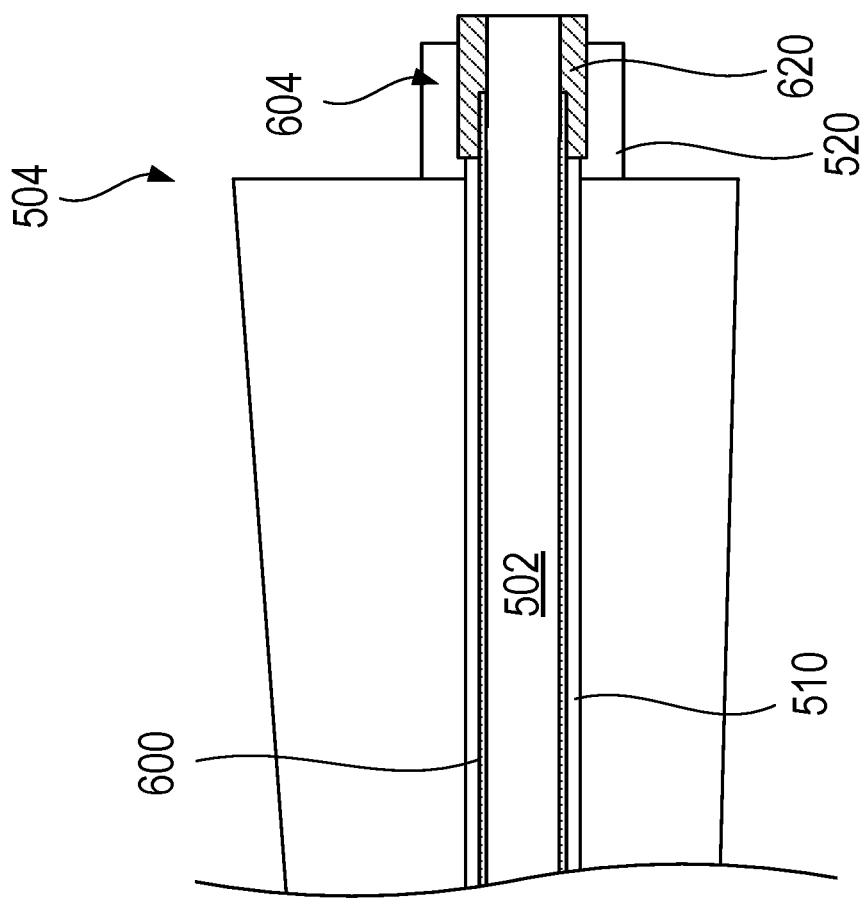
FIGS. 3A-3B illustrate another embodiment of a surgical instrument including a removable working channel in accordance with one or more aspects as described herein.
Figure 3A:
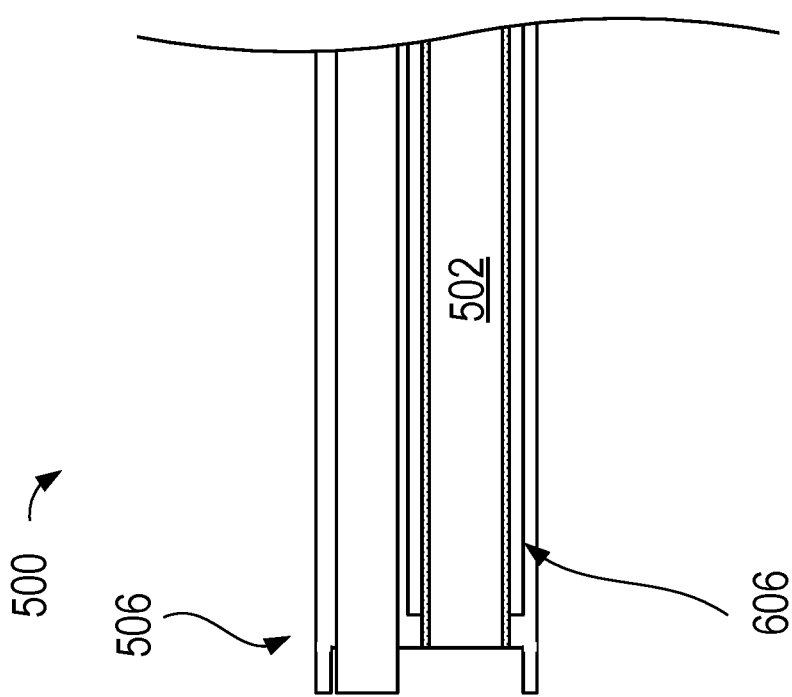
Figure 3B:
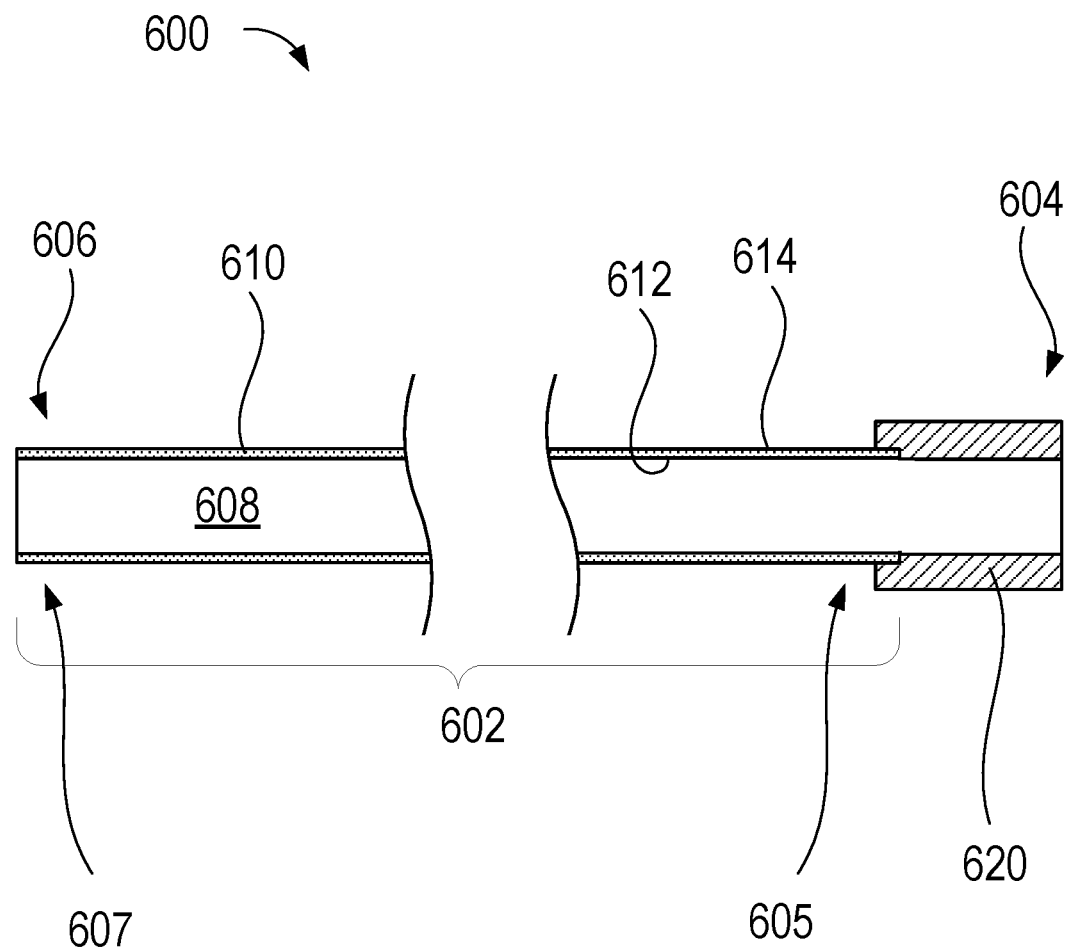

FIGS. 3A-3B illustrate yet another embodiment of a surgical instrument 500 including a removable working channel 600 as described herein, wherein the surgical instrument does not comprise one or more coupling members at or near the distal portion 506 of the surgical instrument 500. FIG. 3A illustrates a cross-sectional view of the surgical instrument 500 as described herein. FIG. 3B illustrates a cross-sectional view of the removable working channel 600 as described herein. FIGS. 3A-3B are discussed together in portions of the description below due to the overlap of depicted features.

In FIGS. 3A-3B, components that can be similar to components described above with reference the embodiment of FIGS. 1A-1E and the description above are identified by similar numbers wherein the reference number used is preceded by the numbers "5" and "6" instead of "1" and "2", respectively. For example, components 502, 504 and 506 can be similar to components 102, 104 and 106, and components 602, 604 and 606 can be similar to components 202, 204 and 206. Reference can be made to the description above for additional descriptions and embodiments of these components which can be used with the embodiment of FIGS. 3A-3B.

With reference to FIG. 3A, the surgical instrument 500 may include at least one instrument channel 502 extending along its longitudinal length. Similar to the surgical instrument 100 of FIGS. 1A-1E, the instrument channel 502 of the surgical instrument 500 is configured to receive the removable working channel 600 such that the removable working channel 600 can be inserted into and/or removed from the instrument channel 502.

Similar to the surgical instrument 100 of FIGS. 1A-1E, at least a portion of the inner surface of the instrument channel 502 of the surgical instrument 500 is covered with a working channel sheath 510. As shown in FIG. 3A, an outer surface of the working channel sheath 510 interfaces with the inner surface of the instrument channel 502, and an inner surface of the working channel sheath 510 interfaces with the instrument channel 502. The working channel sheath 510 is configured to receive the removable working channel 600 as described herein.

As shown in FIG. 3A, the surgical instrument 500 does not comprise one or more coupling members at or near the distal portion 506 of the surgical instrument 500. Thus, the distal portion 506 of the surgical instrument 500 is not configured to lock or couple to the removable working channel 600. Similar to the surgical instrument 100 of FIGS. 1A-1E, the surgical instrument 500 comprises one or more coupling members 520 at the proximal portion 504 of the surgical instrument 500. The coupling members 520 of the surgical instrument 500 may comprise a removable luer fit component, a clamp, a friction fit component (also known as an interference fit component), a latch, a threaded fit component, a slip fit component, a bayonet, a ball spring or pogo latch, a detent, a magnet, a screw lock, a snap fit component, or an O-ring component.

FIG. 3B illustrates a cross-sectional view of the removable working channel 600. Similar to the removable working channel 200 of FIG. 1B, the removable working channel 600 comprises a shaft 602. The shaft 602 includes a proximal end 605, a distal end 607, and a lumen 608 extending therethrough. The shaft 602 includes a wall 610 comprising an inner surface 612 and an outer surface 614. The inner surface 612 of the shaft 602 defines the lumen 608 extending along the longitudinal length of the shaft 602. The outer surface 614 of the shaft 602, when installed, interfaces with the instrument channel 502 of the surgical instrument (not shown).

The removable working channel 600 further comprises one or more locking members 620 at the proximal region 604 of the removable working channel 600. The locking members 620 of the removable working channel 600 are configured to releasably couple to the coupling members 520 of the surgical instrument 500. In an alternate example, the locking members 620 of the removable working channel 600 are configured to releasably couple to the proximal portion 504 of the surgical instrument 500. The locking members 620 of the removable working channel 600 may comprise a removable luer fit component, a clamp, a friction fit component (also known as an interference fit component), a latch, a threaded fit component, a slip fit component, a bayonet, a ball spring or pogo latch, a detent, a magnet, a screw lock, a snap fit component, or an O-ring component. In contrast, the removable working channel 600 does not comprise one or more locking members at or near the distal region 606 of the removable working channel 600 such that the distal region 606 of the removable working channel 600 is not configured to lock or couple to the distal portion 506 of the surgical instrument 500.

Example Identification Members

Figure 4:
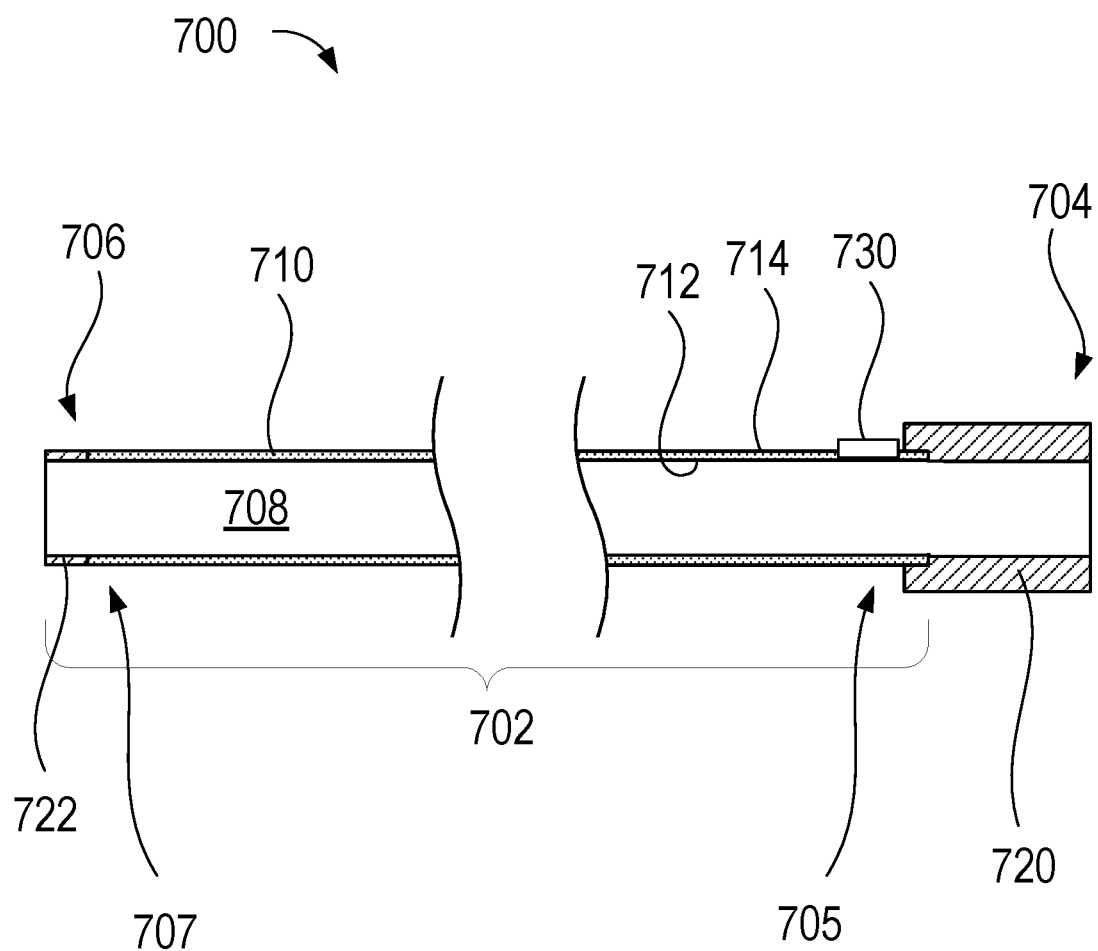
FIG. 4 illustrates another embodiment of a removable working channel in accordance with one or more aspects as described herein.

FIG. 4 illustrates another embodiment of a removable working channel 700 as described herein, wherein the removable working channel 700 further comprises an identification member 730.

In FIG. 4, components that can be similar to components described above with reference the embodiment of FIG. 1B and the description above are identified by similar numbers wherein the reference number used is preceded by the numbers "7" instead of "2", respectively. For example, components 702, 704 and 706 can be similar to components 202, 204 and 206, respectively. Reference can be made to the description above for additional descriptions and embodiments of these components which can be used with the embodiment of FIG. 4.

Similar to the removable working channel 200 of FIG. 1B, the removable working channel 700 comprises a shaft 702 including a proximal end 705, a distal end 707, and a lumen 708 extending therethrough. The shaft 702 includes a wall 710 comprising an inner surface 712 and an outer surface 714. The inner surface 712 of the shaft 702 defines the lumen 708 extending along the longitudinal length of the shaft 702. The outer surface 714 of the shaft 702, when installed, interfaces with the instrument channel of the surgical instrument (not shown). In some embodiments, the removable working channel 700 may further comprise one or more locking members 720 at the proximal region 704 of the removable working channel 700 and/or one or more locking members 722 at the distal region 706 of the removable working channel 700. The locking members 720 and/or 722 of the removable working channel 700 are configured to releasably couple to the surgical instrument (not shown) as described above. The locking members 720 and/or 722 of the removable working channel 700 may comprise a removable luer fit component, a clamp, a friction fit component (also known as an interference fit component), a latch, a threaded fit component, a slip fit component, a bayonet, a ball spring or pogo latch, a detent, a magnet, a screw lock, a snap fit component, or an O-ring component.

With reference to FIG. 4, the removable working channel 700 further comprises one or more identification members 730 configured to store data comprising information regarding the surgical instrument (e.g., one similar to the surgical instrument 100), the removable working channel 700, or both. In some embodiments, the identification member 730 may be attached to the shaft 702 (e.g., on the inner surface 712 or the outer surface 714), or to the locking members 720 and/or 722. Examples of the identification members 730 may include, but not be limited to, a radio-frequency identification (RFID) tag, a near field communication (NFC) tag, a bar code, a Quick Response (QR) code, a Bluetooth low energy (BLE) tag, an ultrasound identification tag, an infrared identification tag, or a video identification tag. The data saved in the identification members 730 may include a source, type, material, dimension, manufacture date, expiration date, and/or identification number of the surgical instrument or the removable working channel 700. In some embodiments, one or more identification members 730 may be installed on the surgical instrument, the removable working channel 700, or both. In other embodiments, the surgical instrument, the removable working channel 700, or both may further comprise at least one sensor or detector configured to read data from the identification members 730.

Example Tool to Couple and/or Uncouple Between Removable Working Channel and Surgical Instrument In accordance with one or more aspects of the present disclosure, a tool may be configured to couple and/or uncouple between a removable working channel (e.g., removable working channel 200, 400, or 600 as described above) and a surgical instrument (e.g., surgical instrument 100, 300, or 500 as described above). The removable working channel and/or the surgical instrument may be configured to couple and/or uncouple to each other only through the use of a specific type of the tool. This way, only people with the specific type of the tool may install and/or remove the removable working channel onto/from the surgical instrument.

In some embodiments, the tool may be configured to adjust an attachment between the removable working channel and the surgical instrument. The tool may comprise an actuator configured to engage and actuate at least one of (i) one or more locking members (e.g., locking members 220, 420, and/or 620 as described above) at the proximal region of the removable working channel and (ii) one or more coupling members (e.g., coupling members 120, 320, and/or 520 as described above) at the proximal portion of the surgical instrument. In another embodiment, the actuator may be configured to engage and actuate at least one of (i) one or more locking members (e.g., locking members 222 and/or 422 as described above) at the distal region of the removable working channel and (ii) one or more coupling members (e.g., coupling members 122 and/or 322 as described above) at the distal portion of the surgical instrument.

The engagement and actuation of the at least one of (i) one or more locking members and (ii) one or more coupling members by the actuator facilitates locking and/or unlocking an attachment between the removable working channel and the surgical instrument. In another embodiment, the tool may be configured to wirelessly communicate with the one or more locking members of the removable working channel to engage or actuate the one or more locking members. In yet another embodiment, the tool may be configured to wirelessly communicate with the one or more coupling members of the surgical instrument to engage or actuate the one or more coupling members. Examples of the tool include, and are not limited to, a key, a driver, a pipe, a needle, and a transmitter.

In some embodiments, the actuator of the tool may be configured to be able to engage only with a certain type or types of the locking members and/or the coupling members. Such an exclusive engagement may be enabled by (1) physical features of the actuator, the locking members, and/or the coupling members or (2) electronic or wireless communications between the tool and the locking members or the coupling members. For example, in one embodiment, the actuator of the tool may have a physical shape that can engage with only a certain type or types of the locking members and/or the coupling members. In another embodiment, the tool may be configured to wirelessly communicate with the locking members and/or the coupling members to allow engagement with only a certain type or types of the locking members and/or the coupling members.

Example Method for Sanitizing or Replacing Removable Working Channels of Surgical Instrument With the removable working channel and the surgical instrument described herein, a user may sanitize or replace the surgical instrument by removing a removable working channel installed in an instrument channel of the surgical instrument, checking the integrity of the removable working channel, and then either (1) cleaning and reinstalling the removable working channel or (2) replacing the removable working channel with a new removable working channel in the surgical instrument, depending on the integrity of the first removable working channel.

Figure 5:
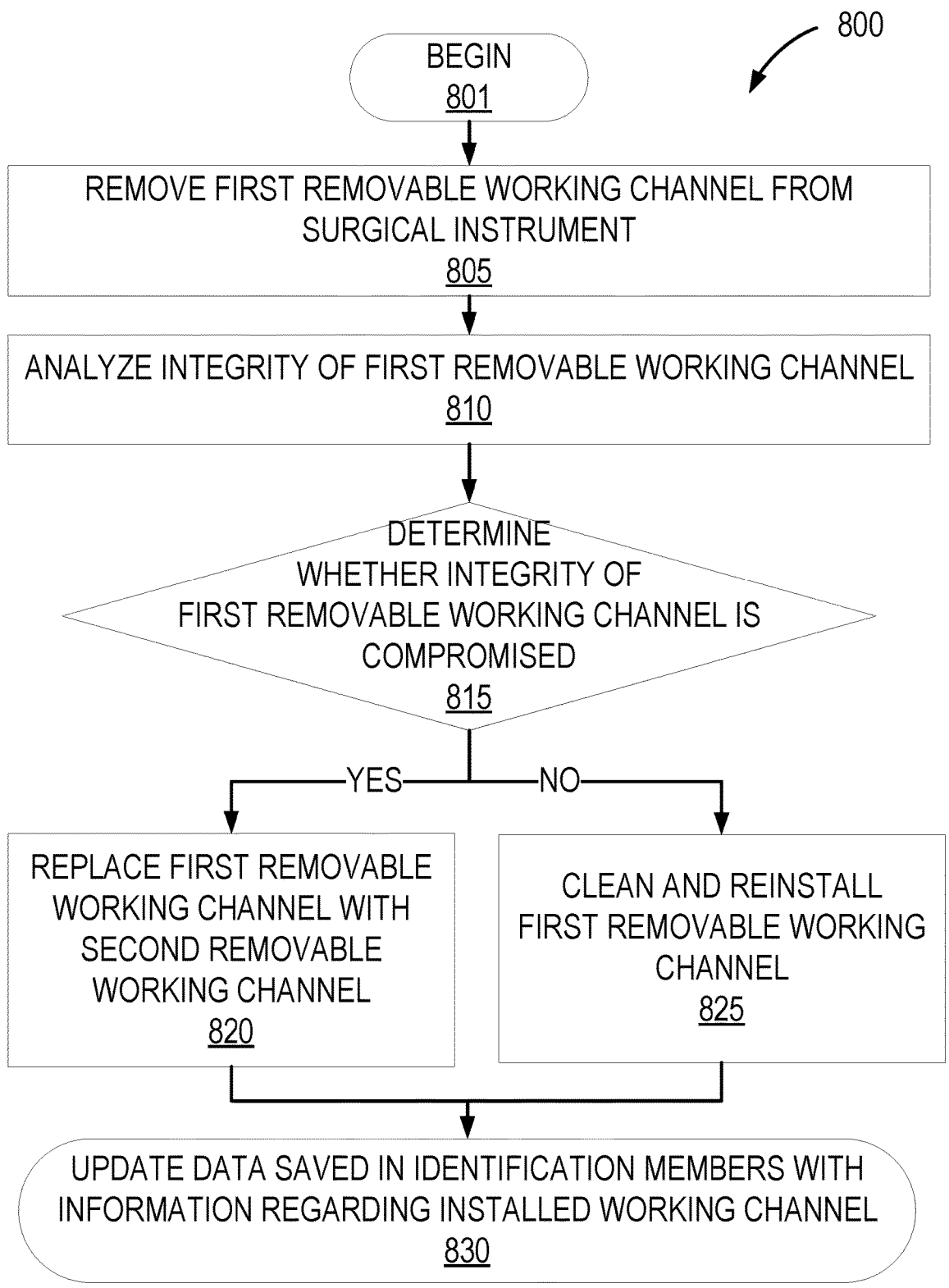
FIG. 5 illustrates a flowchart of an example methodology of replacing and/or cleaning a removable working channel of a surgical instrument.

FIG. 5 depicts a flowchart illustrating an embodiment of a process 800 of sanitizing or replacing one or more removable working channels (e.g., removable working channels 200, 400, 600, and 700 as described above) of a surgical instrument described herein (e.g., surgical instruments 100, 300, and 500 as described above), wherein the process 800 may be conducted by a user. The user may include, but not be limited to, hospitals, physicians, healthcare practitioners, third-party cleaning service companies, medical device companies, and/or autonomous systems. The process 800 may also be implemented, entirely or in part, by an automated system (e.g., robotic system). It will be appreciated that although components described in the process 800 may be identified by the reference numbers used for the embodiment of FIGS. 1A-1E, these components are not limited to the embodiment of FIGS. 1A-1E.

At block 805, the user (e.g., a human operator or an autonomous system) may remove a first removable working channel from a surgical instrument. For example, in implementations in which the removable working channel 200 is installed in the instrument channel 102 of the surgical instrument 100, removing the first removable working channel may comprise removing the removable working channel 200 out of the proximal end of the instrument channel 102. In implementations in which the surgical instrument 100 comprises one or more coupling members 120 and/or 122, and the first removable working channel 200 comprises one or more locking members 220 and/or 222, which are configured to releasably couple to the one or more coupling members 120 and/or 122 of the surgical instrument 100, respectively, block 805 may involve (1) engaging a tool to at least one of (i) the one or more coupling members 120 and/or 122 of the surgical instrument 100 and (ii) the one or more locking members 220 and/or 222 of the first removable working channel 200; (2) actuating the tool to release the one or more coupling members 120 and/or 122 of the surgical instrument 100 from the one or more locking members 220 and/or 222 of the first removable working channel 200; and (3) removing the first removable working channel 200 from the surgical instrument 100.

At block 810, the user may analyze the integrity of the first removable working channel. In some implementations, the user may check the duration of usage of the first removable working channel 200. For example, the user may check the duration of usage of the first removable working channel 200 by accessing data from one or more identification members attached to the first removable working channel 200 (e.g., identification members 730 or one or more RFID tags). At block 815, the user may determine whether the integrity of the first removable working channel is compromised. In some implementations, the standard(s) or factor(s) for deciding whether the removable working channel 200 is compromised may be pre-determined by the user. Additionally or alternatively, the determination of whether the integrity of the first removable working channel is compromised may be determined based on detecting cases of wear and tear, such as areas that include scrapes, holes, or any other signs of wear and tear.

At block 820, if the user determines that the integrity of the first removable working channel is compromised, the user may replace the first removable working channel with a second removable working channel in the instrument channel of the surgical instrument. In some implementations, replacing the first removable working channel with the second removable working channel may involve inserting the distal region 206 of the second removable working channel 200 through the proximal end of the instrument channel 102 of the surgical instrument 100 until the distal region 206 of the second removable working channel 200 reaches near the distal end of the instrument channel 102. In implementations in which the second removable working channel 200 comprises one or more locking members 220 and/or 222, and the surgical instrument 100 comprises one or more coupling members 120 and/or 122, block 820 may involve inserting the distal region 206 of the second removable working channel 200 through the proximal end of the instrument channel 102 of the surgical instrument 100 until at least one of the one or more coupling members 120 and/or 122 of the surgical instrument 100 engages with at least one of the one or more locking members 220 and/or 222 of the second removable working channel 200.

Alternatively, at block 825, if the user determines that the integrity of the first removable working channel is not compromised, the user may clean and reinstall the first removable working channel in the instrument channel of the surgical instrument. In some implementations, reinstalling the first removable working channel 200 in the instrument channel 102 of the surgical instrument 100 may involve inserting the distal region 206 of the first removable working channel 200 through the proximal end of the instrument channel 102 of the surgical instrument 100 until the distal region 206 of the first removable working channel 200 reaches or is near the distal end of the instrument channel 102. In implementations in which the first removable working channel 200 comprises one or more locking members 220 and/or 222, and the surgical instrument 100 comprises one or more coupling members 120 and/or 122, reinstalling the first removable working channel 200 in the instrument channel 102 of the surgical instrument 100 may involve inserting the distal region 206 of the first removable working channel 200 through the proximal end of the instrument channel 102 of the surgical instrument 100 until at least one of the one or more coupling members 120 and/or 122 of the surgical instrument 100 engages with at least one of the one or more locking members 220 and/or 222 of the first removable working channel 200.

At block 830, for a removable working channel (e.g., removable working channel 800) or a surgical instrument including one or more identification members (e.g., identification members 730), the user may optionally update data saved in the identification members with information regarding the installed working channel. Depending on whether the first removable working channel was replaced with the second removable working channel in block 820 or the first removable working channel was cleaned and replaced in block 825, the information regarding the installed working channel may include information as to whether the first removable working channel is reinstalled in the surgical instrument (e.g., surgical instrument 100) or the second removable working channel is installed in the surgical instrument. In the case where the identification member is a RFID tag, the user may use an RFID writer to update a data structure in the RFID tag that specifies whether the removable working channel has been replaced, a date that the removable working channel has been replaced, a count associated with a number of times the working channel has been sanitized but not replaced, or any other suitable data associated with the use or replacement of a removable working channel with respect to a surgical instrument.

Implementing Systems and Terminology

Implementations disclosed herein provide systems, methods and apparatus for increasing a service life of a surgical instrument. More specifically, implementations of the present disclosure relate to a removable working channel for a surgical instrument and to a surgical instrument configured to receive and interfere with the removable working channel.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present disclosure. Various modifications to these implementations will be readily apparent to those skilled in the art, and the generic principles defined herein may be applied to other implementations without departing from the scope of the present disclosure. For example, it will be appreciated that one of ordinary skill in the art will be able to employ a number corresponding alternative and equivalent structural details, such as equivalent ways of fastening, mounting, coupling, or engaging tool components, and equivalent mechanisms for producing particular actuation motions. Thus, the present disclosure is not intended to be limited to the implementations shown herein but is to be accorded the widest scope consistent with the principles and novel features disclosed herein.

What is claimed is:

1. A removable working channel of a surgical instrument, the surgical instrument extending from a proximal end to a distal end and having a working channel sheath configured to receive the removable working channel, the removable working channel comprising:
   a shaft, comprising:
      a proximal region and a distal region, the distal region of the shaft being located proximal relative to the distal end of the surgical instrument when the removable working channel is received within the working channel sheath;
      an inner surface defining a lumen extending through the shaft, wherein the inner surface is configured to allow passage of a medical tool through the shaft to extend outward beyond the distal end of the surgical instrument; and
      an outer surface having a substantially circular cross-section and configured to interface with the working channel sheath of the surgical instrument, wherein a diameter of the outer surface of the shaft is substantially the same as a diameter of an inner surface of the working channel sheath; and
   a first locking member comprising a luer fit or a threaded fit component, the first locking member at the proximal region of the shaft, the first locking member configured to releasably couple to the proximal end of the surgical instrument.

2. The removable working channel of claim 1, wherein the surgical instrument comprises an endoscope.

3. The removable working channel of claim 1, further comprising a second locking member at the distal region of the shaft.

4. The removable working channel of claim 3, wherein the second locking member comprises an annular ring or a spring clamp at the distal region of the shaft.

5. The removable working channel of claim 3, wherein the second locking member comprises at least one of a clamp, a friction fit component, a latch, a snap fit component, a screw lock, a luer fit, a threaded fit component, a slip fit component, a bayonet, a ball spring or pogo latch, a detent, a magnet, and an O-ring component.

6. The removable working channel of claim 1, wherein the removable working channel does not comprise a locking member at the distal region of the shaft.

7. The removable working channel of claim 1, further comprising at least one identification member configured to store data comprising information regarding a source of the removable working channel.

8. The removable working channel of claim 7, wherein the at least one identification member comprises a radio-frequency identification (RFID) tag.

9. The removable working channel of claim 1, wherein the shaft is made of extruded plastic.

10. The removable working channel of claim 1, wherein the shaft further comprises an inner liner attached to the inner surface of the removable working channel.

11. The removable working channel of claim 10, wherein the inner liner is made of polytetrafluoroethylene (PTFE), high-density polyethylene (HDPE), low-density polyethylene (LDPE), linear low density poly ethylene (LLDPE), or hydrophilic materials.

12. The removable working channel of claim 1, wherein the shaft comprises a reinforcement member disposed at least partially between the inner surface of the removable working channel and the outer surface of the removable working channel.

13. The removable working channel of claim 12, wherein the reinforcement member comprises at least one of (i) one or more coils, (ii) one or more braids, and (iii) one cable tube.

14. The removable working channel of claim 1, wherein the shaft is parallel to a longitudinal axis of the surgical instrument when the removable working channel is received within the working channel sheath.

15. A surgical instrument configured to receive a removable working channel, the surgical instrument comprising:
a proximal end and a distal end;
an instrument channel extending through the proximal and distal end, the instrument channel comprising:
a proximal region and a distal region; and
a first inner surface defining a lumen extending through the instrument channel;
a working channel sheath attached to the first inner surface of the instrument channel and configured to interface with the removable working channel; and
a first coupling member comprising a luer fit or a threaded fit component, the first coupling member at the proximal end of the surgical instrument, the first coupling member configured to releasably couple to a proximal region of the removable working channel, the removable working channel further including a distal region located proximal relative to the distal end of the surgical instrument when the removable working channel is received within the working channel sheath,
wherein the removable working channel comprises a second inner surface configured to allow passage of a medical tool through the instrument channel to extend outward beyond the distal end of the surgical instrument when the removable working channel is received within the working channel sheath, and
wherein an outer surface of the removable working channel has a substantially circular cross-section and a diameter that is substantially the same as a diameter of the first inner surface.

16. The surgical instrument of claim 15, further comprising a second coupling member at the distal end of the surgical instrument, the second coupling member configured to releasably couple to the distal region of the removable working channel.

17. The removable working channel of claim 15, wherein the working channel sheath is made of extruded plastic.

18. The surgical instrument of claim 15, wherein the working channel sheath comprises an inner liner made of polytetrafluoroethylene (PTFE), high-density polyethylene (HDPE), low-density polyethylene (LDPE), or linear low density poly ethylene (LLDPE).

19. The surgical instrument of claim 15, wherein the working channel sheath comprises at least one of (i) one or more coils, (ii) one or more braids, and (iii) one cable tube.

20. The surgical instrument of claim 15, wherein the coils, the braids, or the cable tubes are at least partially made of stainless steel, copper, other metals, Nitinol alloy, graphite, polyparaphenylene terephthalamide, Ultra-high-molecular-weight polyethylene (UHMWPE), PEEK, or nylon.

21. The surgical instrument of claim 15, further comprising at least one detector configured to read data from at least one identification member of the removable working channel, the data comprising information regarding a source of the removable working channel.

\* \* \* \* \*